United States Patent
Brynelsen et al.

(10) Patent No.: US 8,214,049 B2
(45) Date of Patent: Jul. 3, 2012

(54) GASTRIC STIMULATION SYSTEMS AND METHODS UTILIZING A TRANSGASTRIC PROBE

(75) Inventors: Charles R. Brynelsen, Menlo Park, CA (US); Michael F. Wei, Redwood City, CA (US); Kurt D. Sparks, San Carlos, CA (US); Kenneth L. Wong, Saratoga, CA (US); George Pool, El Dorado Hills, CA (US)

(73) Assignee: Intrapace Inc., Mountain View, CA (US)

( * ) Notice: Subject to any disclaimer, the term of this patent is extended or adjusted under 35 U.S.C. 154(b) by 623 days.

(21) Appl. No.: 12/176,950

(22) Filed: Jul. 21, 2008

(65) Prior Publication Data
US 2009/0030475 A1    Jan. 29, 2009

Related U.S. Application Data

(60) Provisional application No. 60/951,909, filed on Jul. 25, 2007.

(51) Int. Cl.
*A61N 1/05* (2006.01)

(52) U.S. Cl. .......... 607/40; 607/1; 607/2; 607/115; 607/116; 607/130; 607/133

(58) Field of Classification Search ............ 607/1–2, 607/40, 115–116, 130, 133
See application file for complete search history.

(56) References Cited

U.S. PATENT DOCUMENTS

| | | | |
|---|---|---|---|
| 4,592,339 A | 6/1986 | Kuzmak et al. |
| 5,263,480 A | 11/1993 | Wernicke et al. |
| 5,438,985 A | 8/1995 | Essen-Moller |
| 5,855,614 A | 1/1999 | Stevens et al. |
| 5,865,843 A | 2/1999 | Baudino |
| 6,027,523 A | 2/2000 | Schmieding |
| 6,091,992 A | 7/2000 | Bourgeois et al. |
| 6,535,764 B2 | 3/2003 | Imran et al. |
| 6,684,104 B2 | 1/2004 | Gordon et al. |
| 6,826,428 B1 | 11/2004 | Chen et al. |
| 6,895,278 B1 | 5/2005 | Gordon |

(Continued)

FOREIGN PATENT DOCUMENTS
WO    WO 2006/083885 A1    8/2006
(Continued)

OTHER PUBLICATIONS
U.S. Appl. No. 10/109,296; first named inventor: Mir Imran, filed Mar. 26, 2002.
(Continued)

*Primary Examiner* — Carl H Layno
*Assistant Examiner* — Deborah Malamud
(74) *Attorney, Agent, or Firm* — Kilpatrick Townsend & Stockton LLP

(57) ABSTRACT

Gastric stimulation devices, systems and methods are provided, particularly for stimulating a gastric organ having an internal cavity. Such devices and systems are typically implanted outside of the gastric organ while the environment of the internal cavity is probed and monitored by one or more sensors. The sensor information may be used to affect the stimulation signals provided to the gastric organ by the devices and systems. Such feedback integration assists in providing treatments and stimulation programs that are tailored to the needs of the individual patient.

29 Claims, 13 Drawing Sheets

U.S. PATENT DOCUMENTS

| | | |
|---|---|---|
| 7,016,735 B2 | 3/2006 | Imran et al. |
| 7,020,531 B1 | 3/2006 | Colliou et al. |
| 7,076,305 B2 | 7/2006 | Imran et al. |
| 7,107,100 B2 | 9/2006 | Imran et al. |
| 7,120,498 B2 | 10/2006 | Imran et al. |
| 7,371,215 B2 | 5/2008 | Colliou et al. |
| 7,502,649 B2 | 3/2009 | Ben-Haim et al. |
| 7,530,943 B2 | 5/2009 | Lechner |
| 2001/0011543 A1 | 8/2001 | Forsell |
| 2002/0072780 A1 | 6/2002 | Foley |
| 2003/0167025 A1 | 9/2003 | Imran et al. |
| 2004/0059393 A1 | 3/2004 | Policker et al. |
| 2004/0147816 A1 | 7/2004 | Policker et al. |
| 2004/0162595 A1 | 8/2004 | Foley |
| 2004/0243195 A1 | 12/2004 | Imran et al. |
| 2005/0065571 A1 | 3/2005 | Imran |
| 2005/0113880 A1 | 5/2005 | Gordon |
| 2005/0143760 A1 | 6/2005 | Imran |
| 2005/0143784 A1 | 6/2005 | Imran |
| 2005/0149142 A1 | 7/2005 | Starkebaum |
| 2005/0222637 A1 | 10/2005 | Chen |
| 2005/0222638 A1 | 10/2005 | Foley et al. |
| 2006/0069414 A1 | 3/2006 | Imran et al. |
| 2006/0074457 A1 | 4/2006 | Imran et al. |
| 2006/0074458 A1 | 4/2006 | Imran |
| 2006/0089699 A1 | 4/2006 | Imran |
| 2006/0111753 A1 | 5/2006 | Imran et al. |
| 2006/0116735 A1 | 6/2006 | Imran et al. |
| 2006/0173238 A1 | 8/2006 | Starkebaum |
| 2007/0299481 A1 | 12/2007 | Syed et al. |
| 2008/0065168 A1 * | 3/2008 | Bitton et al. .................... 607/40 |
| 2008/0161875 A1 | 7/2008 | Stone |
| 2008/0208010 A1 | 8/2008 | Boyden et al. |
| 2009/0054914 A1 | 2/2009 | Lechner |
| 2009/0192404 A1 | 7/2009 | Ortiz et al. |
| 2009/0306462 A1 | 12/2009 | Lechner |
| 2010/0152532 A1 | 6/2010 | Marcotte |
| 2010/0217213 A1 | 8/2010 | Forsell |

FOREIGN PATENT DOCUMENTS

| | | |
|---|---|---|
| WO | WO 2008/063486 A2 | 5/2008 |
| WO | WO 2008/117296 A1 | 10/2008 |
| WO | WO 2008/139463 A2 | 11/2008 |
| WO | WO 2009/048380 A1 | 4/2009 |
| WO | WO 2009/048386 A1 | 4/2009 |

OTHER PUBLICATIONS

International Search Report and Written Opinion of PCT Application No. PCT/US2008/070777, dated Nov. 7, 2008, 11 pages total.

* cited by examiner

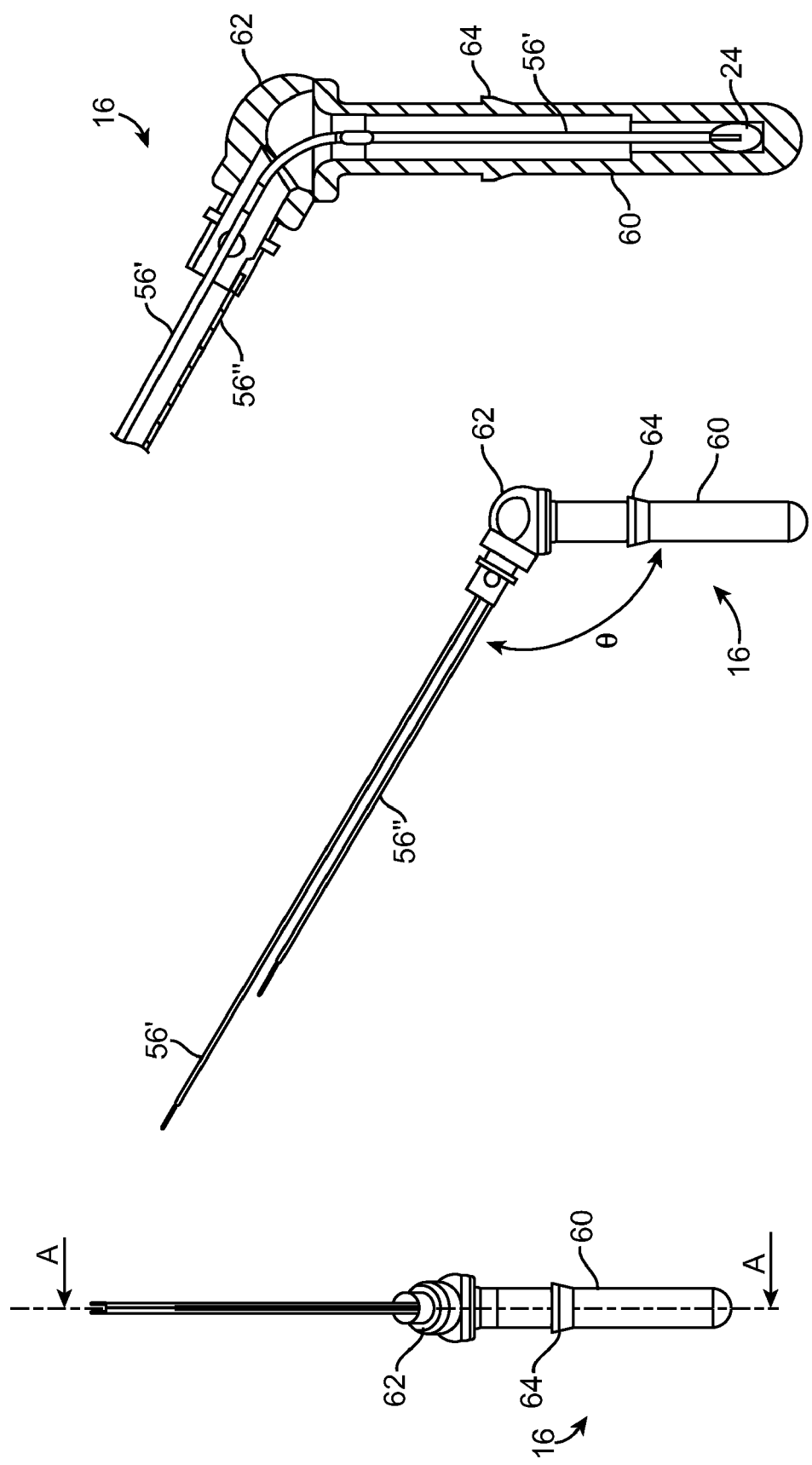

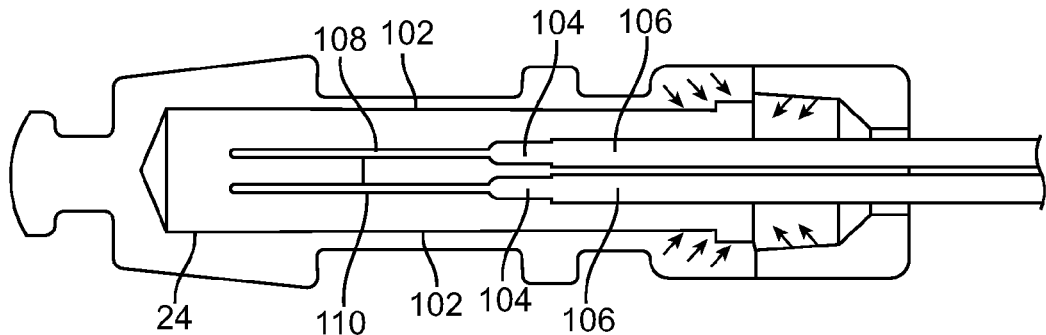
FIG. 11
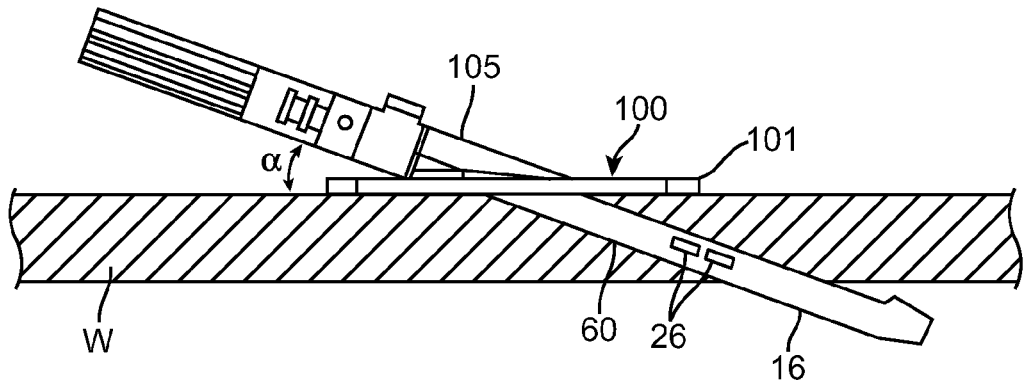
FIG. 12
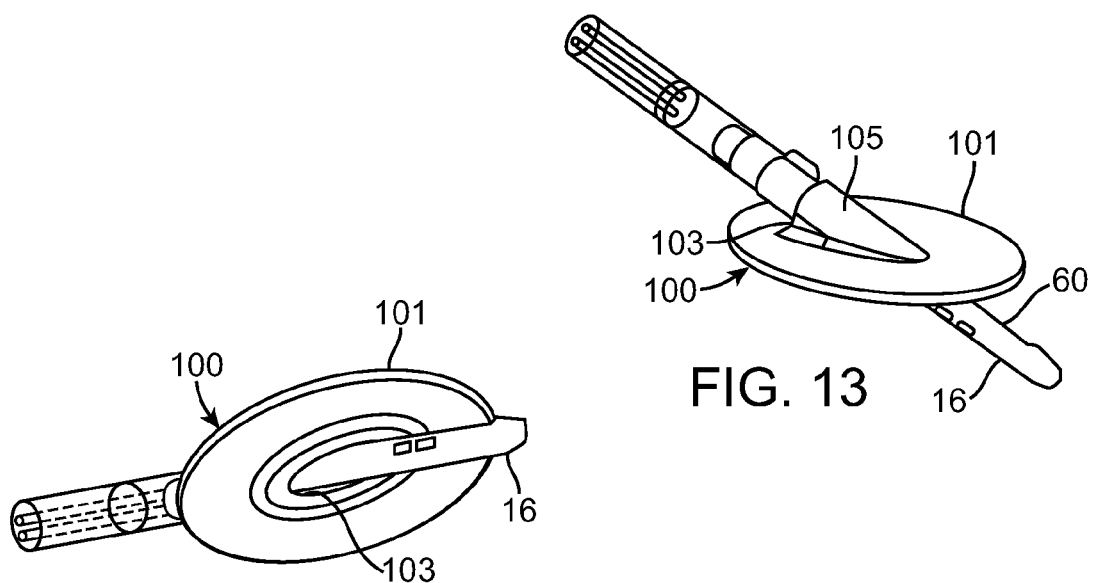
FIG. 13
FIG. 14

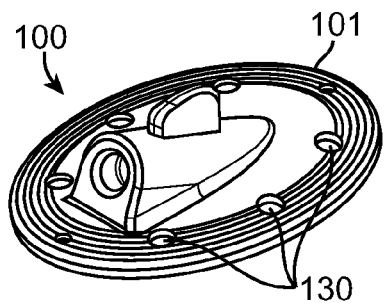
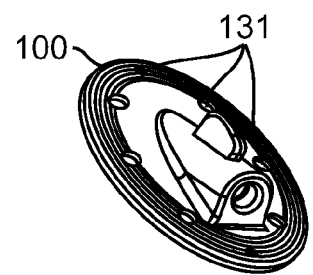
FIG. 15　　　　　　　　FIG. 16
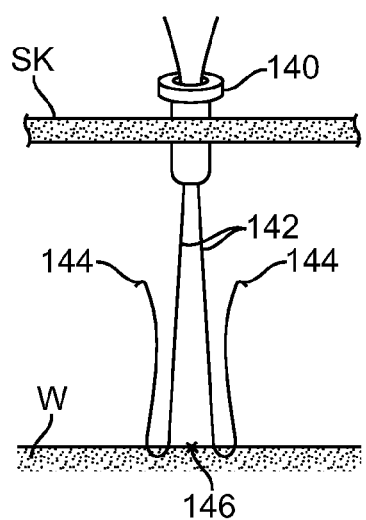
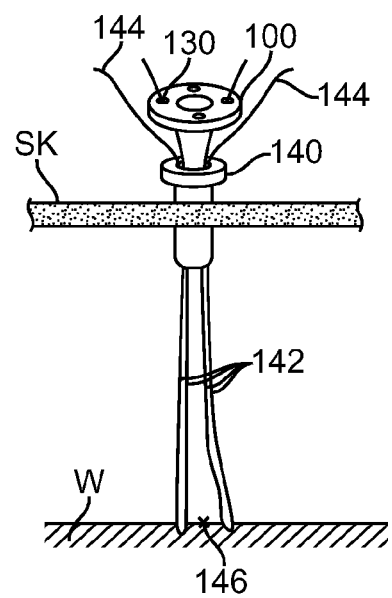
FIG. 17A　　　　　　　　FIG. 17B
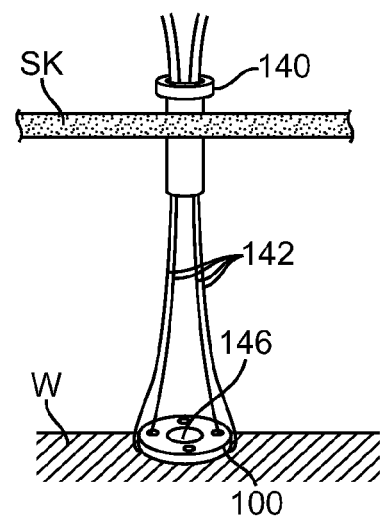
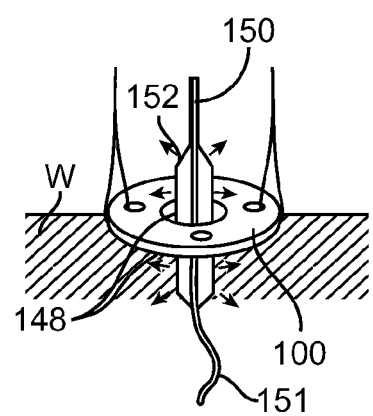
FIG. 17C　　　　　　　　FIG. 17D

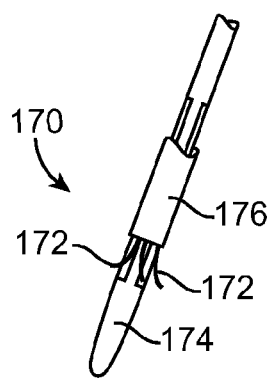
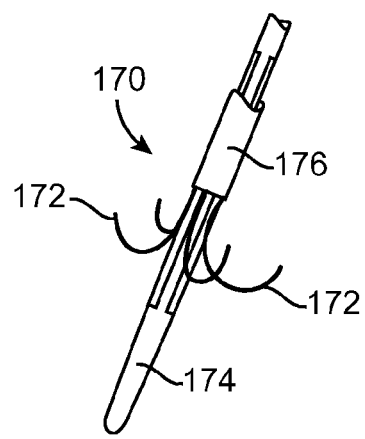
FIG. 25A    FIG. 25B
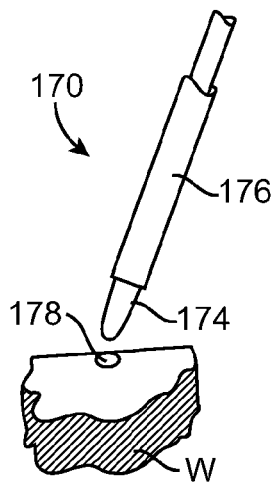
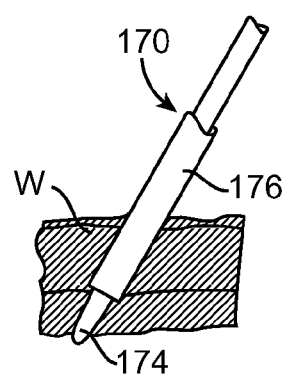
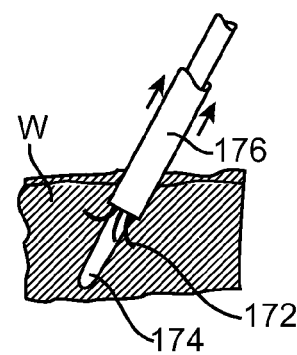
FIG. 26A    FIG. 26B    FIG. 26C
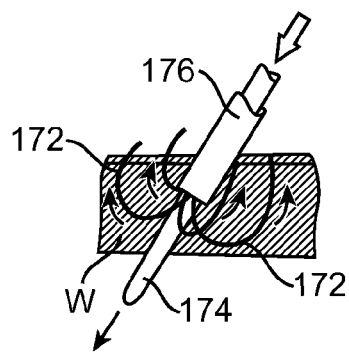
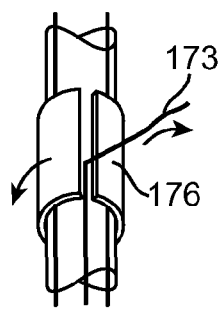
FIG. 26D    FIG. 26E

GASTRIC STIMULATION SYSTEMS AND METHODS UTILIZING A TRANSGASTRIC PROBE

CROSS-REFERENCES TO RELATED APPLICATIONS

This application claims the benefit of under 35 U.S.C. §109(e) of U.S. Provisional Patent Application No. 60/951,909 filed on Jul. 25, 2007, the disclosure of which is incorporated herein by reference.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

Morbid obesity is a chronic lifelong, multi-factorial disorder, causing the patient to have excessive fat deposits and associated medical, psychological, physical, social and economic problems. Obesity is directly correlated with type II diabetes and cardiovascular disease. Etiological factors include the involvement of hereditary, biochemical, hormonal, environmental, behavioral, health and cultural elements. Extreme forms of obesity are unlikely to respond to diet, behavioral therapy or medication alone. As early as 1991, the US National Institute of Health issued a statement recognizing the known lack of success with conservative forms of treatment, noting that operations to constrict or bypass the stomach were justified for fully informed and consenting patients and constituted an acceptable risk. Safe and effective surgical treatment increases the life expectancy and quality of life for some extremely obese individuals.

A variety of surgical procedures have been developed to treat obesity. For example, restrictive operations are performed, such as stomach stapling or gastric banding. In stomach stapling, an incision is made in the abdomen to gain access to the peritoneal cavity. Surgical staples and a plastic band are used to create a small pouch in the fundus region of the stomach. With gastric banding, a small band is placed just distal to the lower esophageal sphincter (LES), creating a small pouch. Alternatively, Roux-en-Y gastric bypass is commonly used. Gastric bypass surgery makes the stomach smaller and allows food to bypass part of the small intestine. Rarely used is a procedure called biliopancreatic diversion. Biliopancreatic diversion changes the normal process of digestion by making the stomach smaller and allowing food to bypass part of the small intestine so that fewer calories are absorbed.

These surgeries impart permanent changes to the patient's anatomy and are associated with a variety of complications. For example, chronic vomiting may occur after surgery. In gastric bypass, the stomach is connected to the bowel and the opening between them is made deliberately small to slow the flow of food out of the small stomach pouch. With healing, scar tissue forms which can sometimes cause further constriction. This may cause the opening between the stomach and the bowel to become so small that food cannot pass through, resulting in repeated vomiting. This complication can be corrected in an outpatient procedure during which the opening is stretched by a balloon inserted through a scope down into the stomach. If unsuccessful, a revisional surgery is required.

Such vomiting after surgery may cause a postoperative hernia. This is due to straining before the incision heals completely. Other causes are infections in the wound or body weight which pulls against the sutures. Hernias occur about 10% to 20% of the time after using a standard incision.

In addition, gastric bypass does not allow for normal absorption of iron, B-12 and calcium because the portion of the digestive system which absorbs these vitamins and minerals is bypassed. Deficiencies in these nutrients can lead to many problems. Iron deficiency causes anemia and weakness. Deficiencies in calcium can cause osteoporosis. Lack of daily B-12 can lead to neurological problems.

Further, patients may also develop bowel obstructions after surgery. Whenever two ends of an incision meet and are sewn together scar tissue forms. This scar tissue can cause adhesions which, in turn, can cause a bowel obstruction. This is a very serious condition that requires immediate attention.

Thus, it would be desired to provide less invasive treatments for obesity and other gastric disorders. Such treatments should avoid anatomical reconfigurations and their associated risks. In addition, such treatments should be capable of being tailored to the needs of the individual patient with few associated risks. At least some of these objectives will be met by the present invention.

BRIEF SUMMARY OF THE INVENTION

Gastric stimulation devices, systems and methods are provided, particularly for stimulating a gastric organ having an internal cavity. Such devices and systems are typically implanted outside of the gastric organ while the environment of the internal cavity is probed and monitored by one or more sensors. The sensor information may be used to affect the stimulation signals provided to the gastric organ by the devices and systems. Such feedback integration assists in providing treatments and stimulation programs that are tailored to the needs of the individual patient.

In a first aspect of the present invention, a lead is provided for stimulating a gastric organ having an internal cavity. In some embodiments, the lead comprises a lead body having a distal end and a transgastric probe disposed near the distal end of the lead body. The probe is configured to be implanted across a wall of the organ so that its distal tip extends into the internal cavity. The lead also includes at least one electrode disposed along the lead body proximal to the transgastric probe, wherein the at least one electrode is engageable with the wall so as to be in electrical contact with the wall. Thus, in this embodiment, the organ may be stimulated by an electrode in a location separate from the transgastric probe. For example, when the organ comprises a stomach, one of the at least one electrodes may be disposed at a location along the lead body which allows the one of the at least one electrodes to engage the wall in a zone near a lesser curvature of the stomach while the probe is implanted near a greater curvature of the stomach. In some embodiments, the lead further comprises at least one electrode disposed along the probe.

Typically, the transgastric probe includes a sensor configured to sense an aspect of the internal cavity. Examples of such sensors include ingestion sensors, temperature sensors, pH sensors, mechanical sensors, strain gauges, contraction sensors, electrical sensors, compositional sensors, impedance sensors, pressure sensors, biochemical sensors, optical emitters and sensors, and the like. Such sensors may be used alone, in plurality or in any combination.

In some embodiments, the transgastric probe has an outer surface exposed to the internal cavity during implantation wherein the outer surface primarily comprises a conductive material. Such a conductive material may be thermally conductive to provide accurate temperature changes to a temperature sensor. Likewise, such a conductive material may be electrically conductive to allow the probe to act as a return electrode.

In some embodiments, the lead body includes an anchoring feature which is attachable to the stomach wall so as to anchor the at least one electrode in engagement with the wall. In some embodiments, the lead further comprises a suture disc disposed along the lead body, wherein the suture disc is positioned so as to be attached to the organ wall while the transgastric probe is implanted. Optionally, the suture disc may position the probe at an angle of less than approximately 90 degrees relative to the wall. The suture disc may also be fixed or removable. In some embodiments, the lead further comprises a buffer disc positionable near the wall while the probe is implanted so as to assist in sealing a transgastric path made by the probe. Optionally, the buffer disc may comprise a tissue adhering material.

In some embodiments, the transgastric probe has an outer surface exposed to the internal cavity during implantation wherein the outer surface primarily comprises a polymer, a flexible polymer, a perfluoro elastomer or a combination of these. In such embodiments, the device may have a variety of the above described additional features.

In a second aspect of the present invention, a system is provided for stimulating a gastric organ having an internal cavity. In some embodiments, the system comprises a lead having a transgastric probe disposed near its distal end, the probe configured to be implanted across a wall of the organ so that its distal tip extends into the internal cavity, and a suture disc removably coupleable with the lead so that the suture disc is attachable to the organ wall while the transgastric probe is implanted. The system further includes at least one electrode disposed along the lead, wherein the at least one electrode is engageable with the wall so as to be in electrical contact with the wall.

In some embodiments, the at least one electrode is disposed along the gastric probe. In other embodiments, the at least one electrode is disposed proximal to the gastric probe. The transgastric probe typically includes a sensor configured to sense an aspect of the internal cavity. Examples of such sensors include ingestion sensors, temperature sensors, pH sensors, mechanical sensors, strain gauges, contraction sensors, electrical sensors, compositional sensors, impedance sensors, pressure sensors, biochemical sensors, optical emitters and sensors, and the like. Such sensors may be used alone, in plurality or in any combination.

In some embodiments, the suture disc is foldable for delivery through a delivery device. In other embodiments, the suture disc positions the probe at an angle of less than approximately 90 degrees relative to the wall. In yet other embodiments, the suture disc obstructs a passageway through at least a portion of the lead when locked in coupled arrangement with the lead.

In another aspect of the present invention, a method is provided for stimulating a gastric organ having an internal cavity. In some embodiments, the method includes advancing a lead toward an outer surface of the gastric organ, the lead having a transgastric probe and at least one electrode, implanting the transgastric probe across a wall of the organ so that its distal tip extends into the internal cavity, and engaging the at least one electrode with the wall so as to be in electrical contact with the wall. The method may also include joining the lead with an implantable pulse generator.

When the at least one electrode is disposed along the lead proximal to the transgastric probe near an anchoring feature, engaging the at least one electrode may comprise attaching the anchoring feature to the outer surface of the organ.

In some embodiments, the method further includes cinching the wall of the organ against the transgastric probe. In some instances, cinching comprises placing a purse string suture around the transgastric probe.

When the organ comprises a stomach, implanting the transgastric probe may comprise implanting the probe across the wall near a greater curvature of the stomach. Likewise, engaging the at least one electrode with the wall may comprise engaging the wall in a zone near a lesser curvature of the stomach.

In some embodiments, advancing the lead comprises approaching the outer surface of the organ with a laparoscopic approach. Or advancing the lead may comprise approaching the outer surface of the organ with a percutaneous endoscopic gastrostomy approach or a modified percutaneous endoscopic gastrostomy approach.

Other objects and advantages of the present invention will become apparent from the detailed description to follow, together with the accompanying drawings

BRIEF DESCRIPTION OF THE DRAWINGS

FIGS. 5A-5C provide various views of an embodiment of a conductive transgastric probe.

FIG. 11 provides a detailed view of a thermistor assembly disposed within a probe as in FIGS. 10A-10B.

FIG. 12 illustrates the transgastric probe of FIG. 10B transecting the stomach wall.

FIGS. 13-14 illustrate a probe passing through a suture disc.

FIG. 15 illustrates a suture disc having suture holes.

FIG. 16 provides a top view illustration of a suture disc wherein sutures are shown attaching the disc to the stomach wall.

FIGS. 17A-17G illustrate example steps of delivering and utilizing a pre-sutured disc.

FIGS. 25A-25B illustrate an embodiment of a needle delivery tool 170.

FIGS. 26A-26E illustrate a needle delivery tool in use.

DETAILED DESCRIPTION OF THE INVENTION

Overview of System

It may be appreciated that the present invention may be used to stimulate any organ having an internal cavity, particularly a gastric organ. Thus, the organ comprises a wall having an inner surface facing the internal cavity and an outer surface facing outwards from the organ. The present invention is described in relation to the stomach for illustration purposes but is not so limited.

Figure 1:
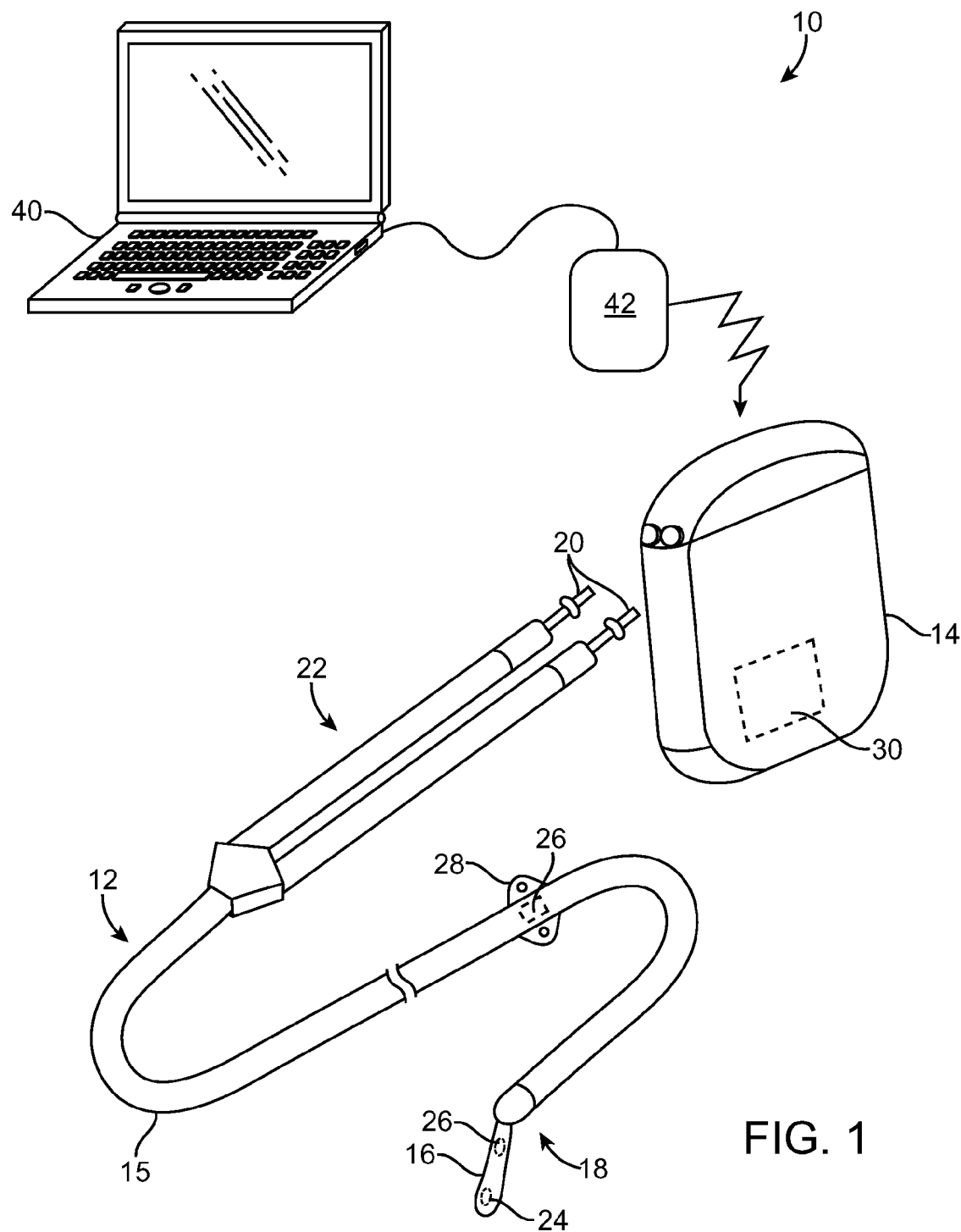
FIG. 1 illustrates an example stimulation system of the present invention.

FIG. 1 illustrates an example stimulation system 10 of the present invention. In this embodiment, the system 10 comprises a lead 12 which is connectable to an implantable pulse generator 14. The lead 12 comprises a lead body 15, a transgastric probe 16 near its distal end 18 and at least one connector 20 near its proximal end 22 for connecting to the pulse generator 14. The transgastric probe 16 is configured to be implanted across the wall of a patient's stomach so that its distal tip extends into the internal cavity. The pulse generator 14 is configured for implantation outside of the stomach. The probe 16 includes at least one sensor 24 that can be used to sense an aspect of the probed environment, in this instance the internal cavity of the stomach. The lead 12 also includes at least one stimulating electrode 26. In some embodiments, the stimulating electrode 26 is disposed along the probe 16, such as in a location so that the electrode 26 resides within the stomach wall or on the surface of the stomach when the probe 16 is positioned therethrough. Thus, the stomach wall is stimulated near the same location as the sensor 24 is taking sensor readings. Alternatively or additionally, the at least one electrode 26 may be located along the lead body 15, proximal to the probe 16. In such embodiments, the electrode 26 contacts the outer surface of the stomach, typically residing thereon but optionally penetrating the stomach wall. In either case, the lead 12 may include anchoring features 28 to assist in holding the electrode 24 in the desired position along the stomach wall.

The system 10, also includes electronic circuitry 30, typically disposed within the pulse generator 14. The electronic circuitry 30 is configured to provide an electrically stimulating signal to the stomach wall via the at least one electrode 26. The electronic circuitry 30 is also configured to receive sensory information from the at least one sensor 24 and optionally utilize the information to affect the stimulating signals. Examples of such sensor based stimulation are provided in U.S. Provisional Patent Application No. 60/947,267, filed on Jun. 29, 2007, incorporated herein by reference for all purposes. While the electrodes 26 are shown in particular configurations and locations, numerous electrode configurations and positions are contemplated. An external computer or programmer 40 may be used to program various stimulation parameters or other instructions into a memory device included with the electronic circuitry 30. The external programmer 40 may be coupled to a telemetry device 42 that communicates with the electronic circuitry 30 via electromagnetic signals.

In the embodiment of FIG. 1, circuitry 30, telemetry device 42, and external programmer 40 are included in a data processing system of the stimulation system 10. Similarly, circuitry 30 may comprise a stand alone data processing system or may be configured to interface with one or more additional electronic components external of (and/or implanted at different locations within) the patient. Generally, the data processing systems included in embodiments of the invention may include at least one processor, which will typically include circuitry implanted in the patient, circuitry external of the patient, or both. When external processor circuitry is included in the data processing system, it may include one or more proprietary processor boards, and/or may make use of a general purpose desktop computer, notebook computer, handheld computer, or the like. The external processor may communicate with a number of peripheral devices (and/or other processors) via a bus subsystem, and these peripheral devices may include a data and/or programming storage subsystem or memory. The peripheral devices may also include one or more user interface input devices, user interface output devices, and a network interface subsystem to provide an interface with other processing systems and networks such as the Internet, an intranet, an Ethernet™, and/or the like. Implanted circuitry of the processor system may have some or all of the constituent components described above for external circuitry, with peripheral devices that provide user input, user output, and networking generally employing wireless communication capabilities, although hard-wired embodiments or other transcutaneous telemetry techniques could also be employed.

An external or implanted memory of the processor system will often be used to store, in a tangible storage media, machine readable instructions or programming in the form of a computer executable code embodying one or more of the methods described herein. The memory may also similarly store data for implementing one or more of these methods. The memory may, for example, include a random access memory (RAM) for storage of instructions and data during program execution, and/or a read only memory (ROM) in which fixed instructions are stored. Persistent (non-volatile) storage may be provided, and/or the memory may include a hard disk drive, a compact digital read only memory (CD-ROM) drive, an optical drive, DVD, CD-R, CD-RW, solid-state removable memory, and/or other fixed or removable media cartridges or disks. Some or all of the stored programming code may be altered after implantation and/or initial use of the device to alter functionality of the stimulator system.

The functions and methods described herein may be implemented with a wide variety of hardware, software, firmware, and/or the like. In many embodiments, the various functions will be implemented by modules, with each module comprising data processing hardware and/or software configured to perform the associated function. The modules may all be integrated together so that a single processor board runs a single integrated code, but will often be separated so that, for example, more than one processor board or chip or a series subroutines or codes are used. Similarly, a single functional module may be separated into separate subroutines or be run in part on separate processor chip that is integrated with another module. Hence, a wide variety of centralized or distributed data processing architectures and/or program code architectures may be employed within different embodiments.

The electronic circuitry comprises and/or is included within a controller or processor for controlling the operations of the device, including sensing, stimulating, signal transmission, charging and/or using energy from a battery device for powering the various components of the circuit, and the like. As such, the processor and battery device are coupled to each of the major components of the implanted circuit. In some embodiments, the electronic circuitry includes an internal clock. The internal clock may also include a real time clock component. The internal clock and/or real time clock may be used to control stimulation, e.g. by stimulating or allowing stimulation at a particular time of the day. The real time clock component may also provide a date/time stamp for detected events that are stored as information in a memory device. Optionally, the memory may be preserved by saving information corresponding to an event of interest which is saved along with the time/date when the event occurred.

In some embodiments, the memory device is configured to store a plurality of code modules for execution by the processor. The code modules provide a variety of determinations based on sensor information and various other inputs, such as information from the internal clock, which are used to actuate a stimulation driver. The stimulation driver is coupled to the stimulating electrodes 26 that are used to provide electrical stimulation.

Figure 2:
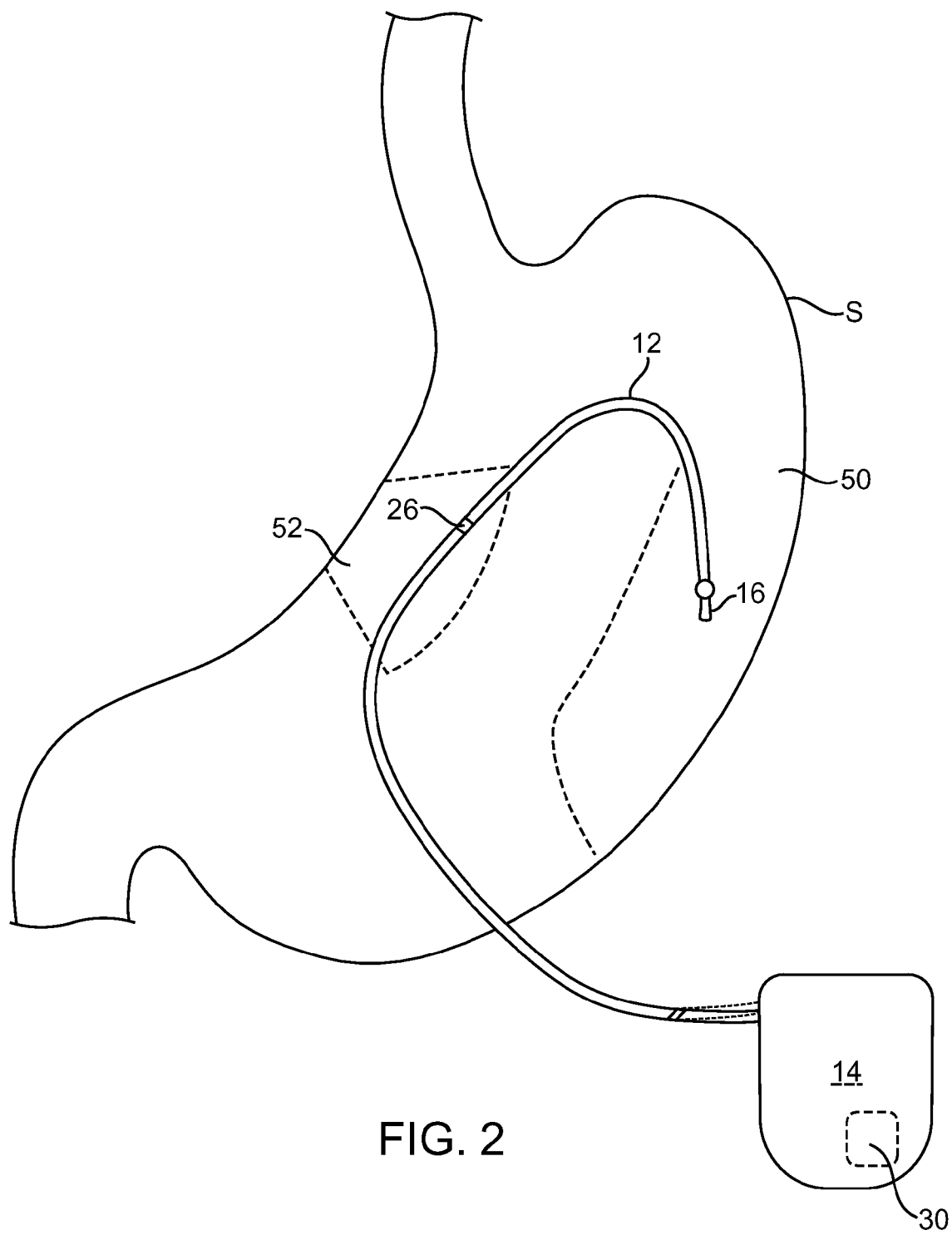
FIG. 2 illustrates example implantation of a stimulation system in relation to a stomach of a patient.

FIG. 2 illustrates example implantation of the stimulation system 10 in relation to a stomach S of a patient. In this example, the pulse generator 14 is implanted outside of the stomach, such as in a soft tissue area of the abdomen, preferably in a subcutaneous pocket. The lead 12 extends from the pulse generator 14 towards the outer surface of the stomach S. The transgastric probe 16 is advanced through the stomach wall at a desired location for sensing the internal environment of the stomach S. In this embodiment, the probe 16 includes a temperature sensor. The temperature sensor is electrically coupled to electronic circuitry 30 for sensing temperatures, temperature changes, rate of temperature changes and other temperature aspects within the stomach Such temperature aspects may be utilized to determine ingestion by the patient which can in turn be used to affect stimulation signals. Therefore, the probe 16 is positioned at a location to most accurately sense temperature changes of the internal environment of the stomach S, including temperature changes due to the temperature of ingested food itself. In this example the probe is positioned generally within a zone 50 near the greater curvature of the stomach. This zone 50 is typically outside of the antrum and fundus regions and located along the lower base of the stomach where food and liquids pass. It may be appreciated that the probe may be positioned in alternative locations along the stomach, such as near the gastro-esophageal junction. Such positioning may allow the probe to sense material as soon as it enters the stomach, before the temperature of the ingested material begins to acclimate to body temperature.

As shown in FIG. 2, the lead 12 is positioned so that a stimulation electrode 26 is disposed along an outer surface of the stomach S. Here, the stimulation electrode 26 is approximately 2-10 inches, more particularly approximately 6 inches, proximal to the probe 16 along the lead body 15, but these dimensions are not so limited. In the example of a 6 inch distance between the electrode 26 and the probe 16, such a distance allows the stimulation electrode 26 to be positioned generally within a zone 52 near the lesser curvature. Particularly, the zone 52 includes a mid-body region biased toward the lesser curvature. More particularly, the zone 52 includes the pes anserinus or gastric nerve bundle, commonly referred to by gastroenterologists as the "crows feet". The range of distances between stimulation electrode and probe allows for many variations of lead configurations and allows sufficient "slack" therebetween as the stomach changes volume from empty to fully distended. Thus, the stimulation electrode 26 may be positioned in alternative locations along the stomach, such as near or within the atrium.

The stimulation electrode intimately contacts the stomach wall and can be secured in position by a variety of methods and devices, including the use of anchoring features 28 such as a bilateral plurality of tabs. These may be secured by laparoscopically placed sutures or by other fixation methods or anchors, such as staples, clips, adhesives, etc. It may be appreciated that, in this example, the distance between the stimulation electrode 26 and the probe 16 along the lead body 15 may be any distance so long as there is sufficient slack between the implanted electrode 26 and probe 16 to allow for inflation, distension or motility of the stomach without substantially applying force to or disturbing the position of the electrode 26 and probe 16. In some embodiments, the straight line distance across the stomach between the implanted electrode 26 and probe 16 is in the range of approximately 2-10 inches.

A variety of lead 12 embodiments are provided herein. Each embodiment includes a variety of features. It may be appreciated that the features depicted in relation to any one embodiment may be utilized in any other embodiment. Further, each of the features may be present in any combination with other features.

Lead Having Conductive Transgastric Probe

Figure 4:
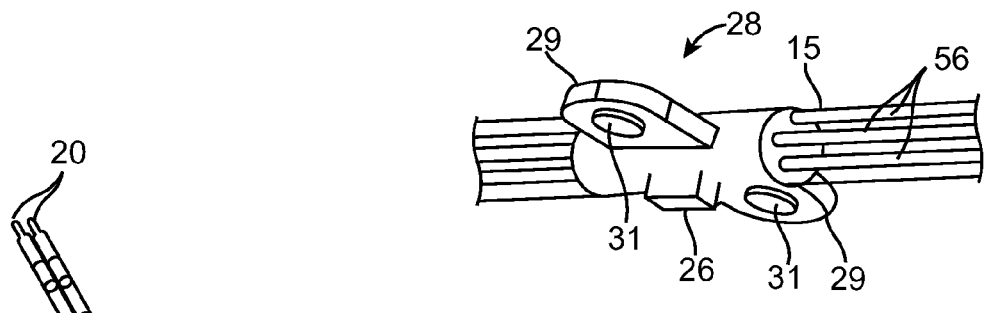
FIG. 4 provides a more detailed view of the stimulating electrode of FIG. 3.
Figure 3:
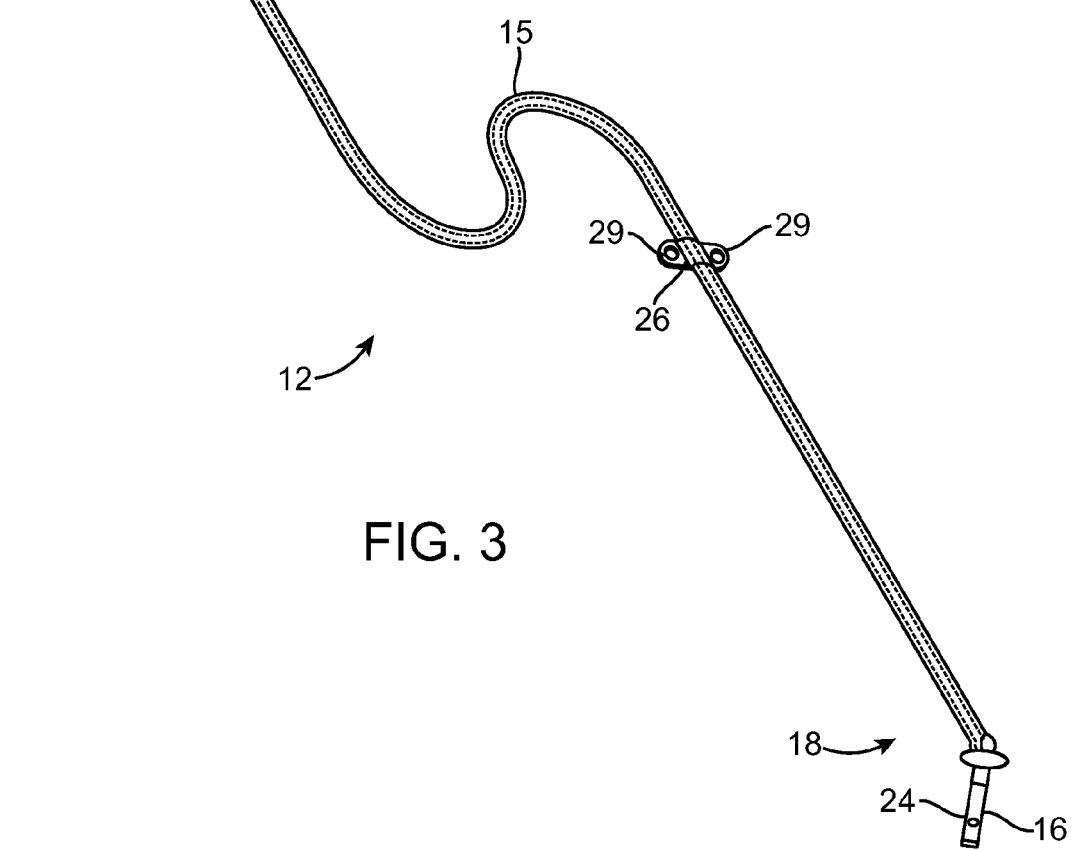
FIG. 3 illustrates an embodiment of a lead of the present invention.

FIG. 3 illustrates an embodiment of a lead 12 of the present invention. As shown, the lead 12 includes a distal end 18 having a transgastric probe 16 and a proximal end 22 having at least one connector 20 which connects with a pulse generator 14 (not shown). In this embodiment, the transgastric probe 16 has an outer surface primarily comprised of a conductive material, such as metal, metal alloy, combination of these or similar material. Examples of such materials include MP35N, steel, stainless steel, titanium, platinum, platinum iridium or other similar material. The material is chosen to be biocompatible and withstand the corrosive environment of the stomach and in some embodiments allows the probe 16 to function as a return electrode. The probe 16 also includes a sensor 24, for sensing temperature in the area of the probe 16. Other aspects of the probe will be described in more detail in later sections. In this embodiment, the lead 12 also includes a stimulating electrode 26 disposed between the distal and proximal ends 18, 22. FIG. 4 provides a more detailed view of the stimulating electrode 26 of FIG. 3. As shown, the electrode 26 is disposed on one side of the lead body 15 so that it may intimately contact the wall of the stomach. In some embodiments, the stimulating electrode has a stimulating surface area in the range of approximately 5 mm$^2$-8 mm$^2$. The return electrode typically has a conductive surface area of approximately 2× to 20× that of the stimulation electrode surface area. This surface area ratio ensures that the current density at the return electrode will not be able to impart significant influence on the stomach wall in which it is in contact with. It may be appreciated that the shape, size and surface of the stimulation electrode 26 may vary to provide effective stimulation, including a single or plurality of stimulation surfaces, flat or curved surfaces, round or shaped electrodes, annular ring(s) or in a continuous exposed coil-like shaped electrode to deliver electrical signals to the tissue in contact.

Also shown are anchoring features 28 to assist in holding the electrode 26 in the desired position along the stomach wall. In this embodiment, the anchoring feature comprises bilateral tabs 29 having apertures 31. The tabs 29 can be secured to the stomach wall by passing sutures through the apertures 31 in a sewing fashion. Alternatively or in addition, the tabs 29 may be pierced at the discretion of the surgeon and sutured to the stomach. Likewise, the tabs 29 may be secured with the use of other fixation methods or anchors, such as with the use of staples, clips, adhesives, T-tags, etc.

Typically, the lead body 15 is comprised of an elongate structure having conductive wires 56 passing therethrough or therealong to couple the various sensors and electrodes disposed along the lead 12 to the connectors 20 and then to the pulse generator 14. In some embodiments, the lead body 15 is comprised of an extruded polymer having one or more lumens, typically wherein each conductive wire passes through a separate lumen. Thus, the conductive wires are insulated from each other, in addition to any individual insulation coating, and are protected from possible damage. Example polymers include thermoset elastomers, such as silicone, thermoform polymers, such as polyurethane, and thermoform elastomers, such as Santoprene®, to name a few.

FIGS. 5A-5C provide various views of the conductive transgastric probe 16. FIGS. 5A-5B illustrate side views of the probe 16. As shown, the probe 16 has an elongate cylindrical portion 60 which joins with a hub 62 which in turn joins with the lead body 15 (not shown). Typically, the cylindrical portion 60 has a length in the range of approximately 15 mm to 25 mm and a diameter in the range of approximately 2 mm to 5 mm, with a preferred diameter of 3 mm, but not so limited Such dimensions are chosen to allow sufficient extension of the cylindrical portion 60 through the stomach wall and into the stomach cavity. In addition, the cylindrical portion 60 has an atraumatic tip, such as having a smooth, rounded shape, to reduce any possibility of acute or chronic injury to the stomach lining.

In this embodiment, the cylindrical portion 60 includes a tissue engagement feature 64. The feature 64 extends radially outwardly and is positioned a distance from the hub 62 to assist in maintaining at least a portion of the stomach wall therebetween. The hub 62 may have a variety of shapes and may be configured to maintain the cylindrical portion 60 at any angle θ in relation to the lead body. For example, in this embodiment the cylindrical portion 60 is disposed at a 110 degree angle in relation to the lead body. It may be appreciated that the angle θ may range from 0 to 180 degrees, however an angle of less than 180 degrees is typically desired to assist in extending the lead body 15 across the outer surface of the stomach. The angle θ and profile of the distal end 18 of the lead typically allows the lead to be delivered through a trocar, cannula or delivery device having an inner diameter of 11 mm or larger.

FIG. 5C provides a cross-sectional view of the transgastric probe 16 of FIGS. 5A-5B. As shown, the cylindrical portion 60 has a hollow construction within which is disposed a sensor 24. It may be appreciated that a plurality of sensors may also be used. In this example, the sensor 24 comprises a thermistor. A variety of temperature sensors can be used, including negative temperature coefficient thermistors, positive temperature coefficient thermistors and thermocouples. In this example, a set of conductive wires 56' extends from the sensor 24, through the hub 62 and through the lead body to the proximal end of the lead. The hollow section of the cylindrical portion 60 is filled with potting material, such as epoxy, to protect and seal the sensor 24 and conductive wires 56' in place. Together with the epoxy, the cylindrical portion 60 and hub 62 create a continuous barrier to protect the thermistor from fluid or other environmental factors. Since in this embodiment the probe 16 is formed from a thermally conductive metal, temperature changes are quickly transferred to the internal thermistor. Further, the electrically conductive metal allows the probe 16 to act as a return electrode. Thus, another conductive wire 56" extends from the probe 16 through the lead body and attaches to the conductive metal to act as a return electrode.

As mentioned above, the transgastric probe 16 is positioned across the stomach wall. The stomach wall is approached from the outside, such as via laparotomy, a laparoscopic approach, a percutaneous endoscopic gastrostomy (PEG) approach or a modified PEG approach. The transgastric path is created with a sharp tip dilator. The dilator has a diameter that is greater than the transgastric probe 16 so as to provide ease of delivery of the probe 16 through the dilated path. The dilator may have a lumen to pass a guidewire across the transgastric path so that the guidewire remains in place after removal of the dilator. The guidewire can then be used as a clear reference path for insertion of the probe 16. Alternatively, an initial transgastric path can be produced with a large bore needle and the tract subsequently increased in diameter via surgical blunt dissection to accept the probe diameter.

Figure 6:
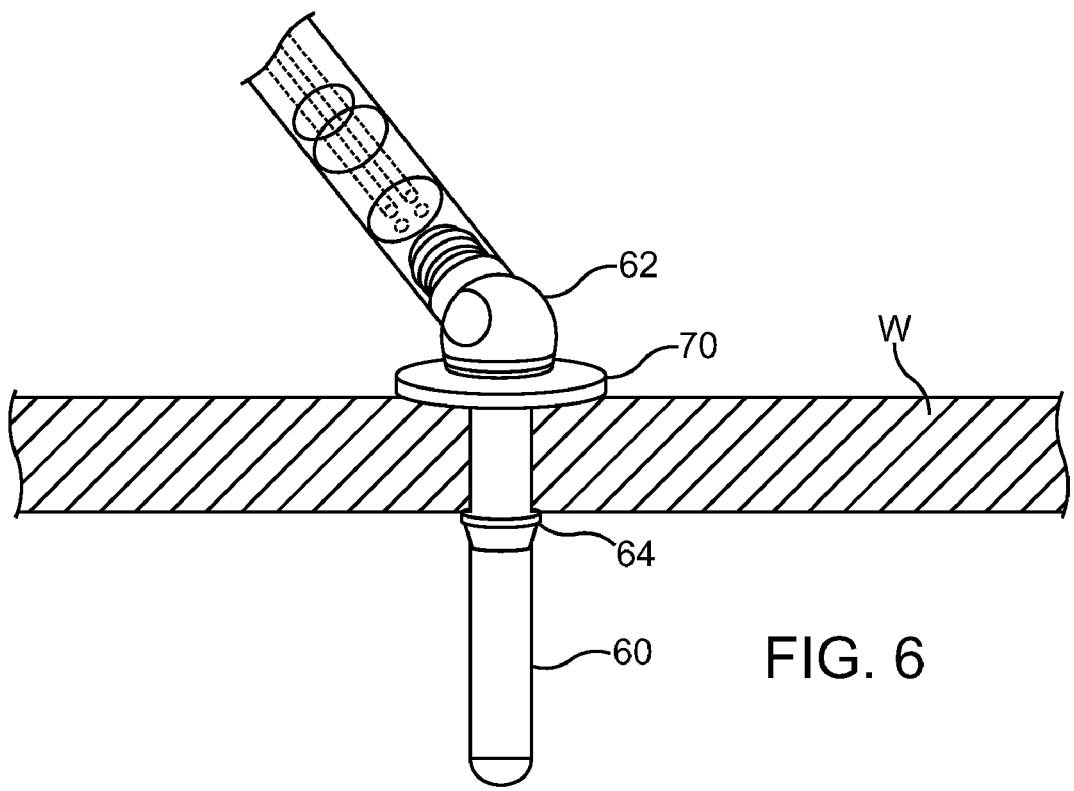
FIG. 6 illustrates an embodiment of a transgastric probe positioned across the stomach wall.

FIG. 6 illustrates the probe 16 positioned across the stomach wall W. In this embodiment, the cylindrical portion 60 includes a tissue engagement feature 64. The feature 64 extends radially outwardly and is positioned a distance from the hub 62 to assist in maintaining the stomach wall therebetween. In other embodiments, the segment of the cylindrical portion 60 that is intended to reside within the stomach wall W has a narrower diameter than the segment intended to reside within the stomach itself. Thus, the lip formed by the increase in diameter acts as a tissue engagement feature 64. It may be appreciated that a variety of designs can be utilized to provide a similar function. In some embodiments, the probe 16 includes graduated markings thereon to facilitate evaluation of penetration depth. And, in some embodiments, the probe 16 includes an inert or steroid coating to reduce inflammation and improve healing stability.

The embodiment of FIG. 6 also includes a tissue sealing buffer disc 70. The buffer disc 70 assists in sealing the transgastric path by encouraging tissue adhesion and ingrowth. Thus, the buffer disc 70 is typically comprised of one or more biostable tissue adhering materials, particularly with a porous or fibrous texture, such as polytetrafluoroethylene (PTFE) or polyester (e.g. Dacron®). The materials may optionally be bioabsorbable. In some embodiments, the buffer disc 70 may optionally be sutured in place.

Figure 7A:
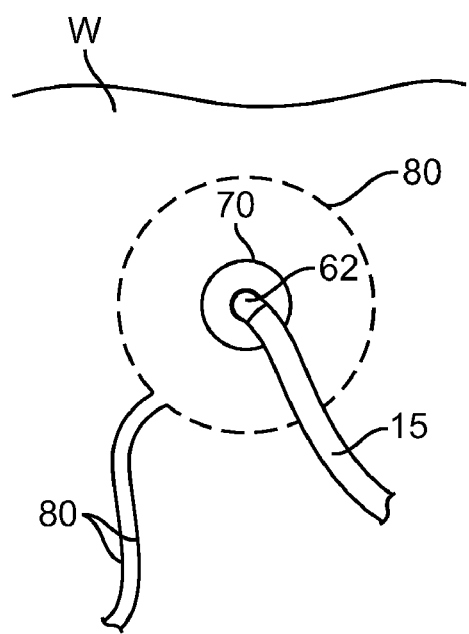
FIGS. 7A-7B provide a top view illustration of the distal end of a lead passing through the stomach wall.
Figure 7B:
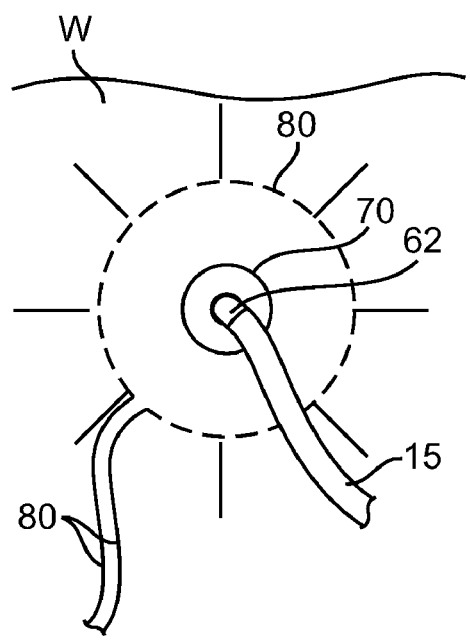

To assist in sealing the transgastric path, the path can be sealed, such as with the use of a purse-string suture. FIGS. 7A-7B provide a top view illustration of the distal end of the lead passing through the stomach wall W. The buffer disc 70 is shown positioned against the surface of the wall W while the hub 62 resides proximal to the disc 70 and the lead body 15 extends proximally therefrom. The transgastric probe 16 is not visible since it extends through the stomach wall W. Purse-string sutures 80 are shown stitched through the tissue of the stomach wall W in an annular arrangement around the transgastric probe 16. FIG. 7A shows the sutures 80 in place. FIG. 7B shows cinching of the sutures 80 to constrict and draw the tissue up against the transgastric probe 16 in a purse-string fashion. Such cinching assists in sealing the transgastric path. In addition, the tissue engagement feature 64 may prevent the probe 16 from being pushed out by the constriction. In some embodiments, the transgastric probe 16 also includes partial or complete circumferential grooves. The sutures 80 are drawn toward or into the grooves to assist in locking the sutures in place.

The buffer disc 70 also provides a compliant load-distributing interface between the more rigid hub 62 and the soft stomach wall W. Thus, the buffer disc 70 typically has a larger diameter than that of the profile of the hub 62. The buffer disc 70 may be of any suitable size, shape and thickness. In some embodiments, the buffer disc has a thickness in the range of approximately 1 to 2 mm.

Figure 8:
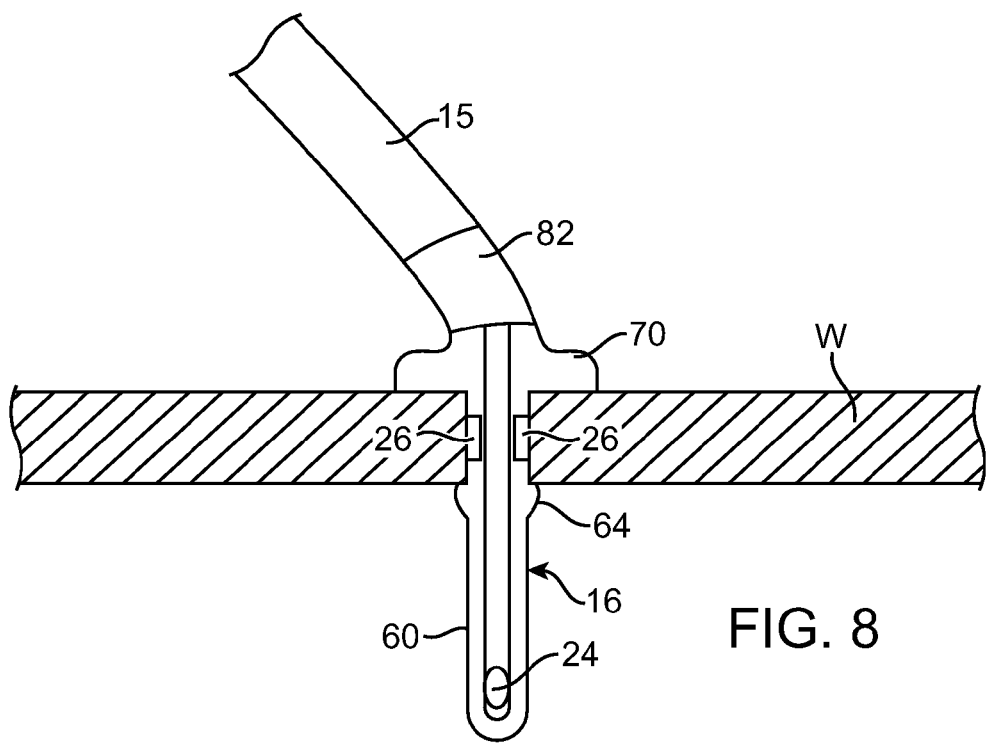
FIG. 8 illustrates an embodiment of the transgastric probe including at least one stimulating electrode in a location so that the electrode resides within the stomach wall when the probe is positioned therethrough.

In some embodiments, at least one stimulating electrode 26 is located within the distal end 18 of the lead 12. This allows stimulation of the wall W near the site of sensing, in addition to or instead of stimulation at a more proximal location along the lead body 15. FIG. 8 illustrates an embodiment of the transgastric probe 16 including at least one stimulating electrode 26 in a location so that the electrode 26 resides within the stomach wall W when the probe 16 is positioned therethrough. Thus, in this embodiment, the at least one electrode 26 is positioned along the elongate cylindrical portion 60 between the tissue engagement feature 64 and the buffer disc 70. To ensure a proper return path for the stimulation energy, a return electrode 82 is disposed at a proximal location along the lead 12.

Lead Having Polymer Transgastric Probe

Figure 9:
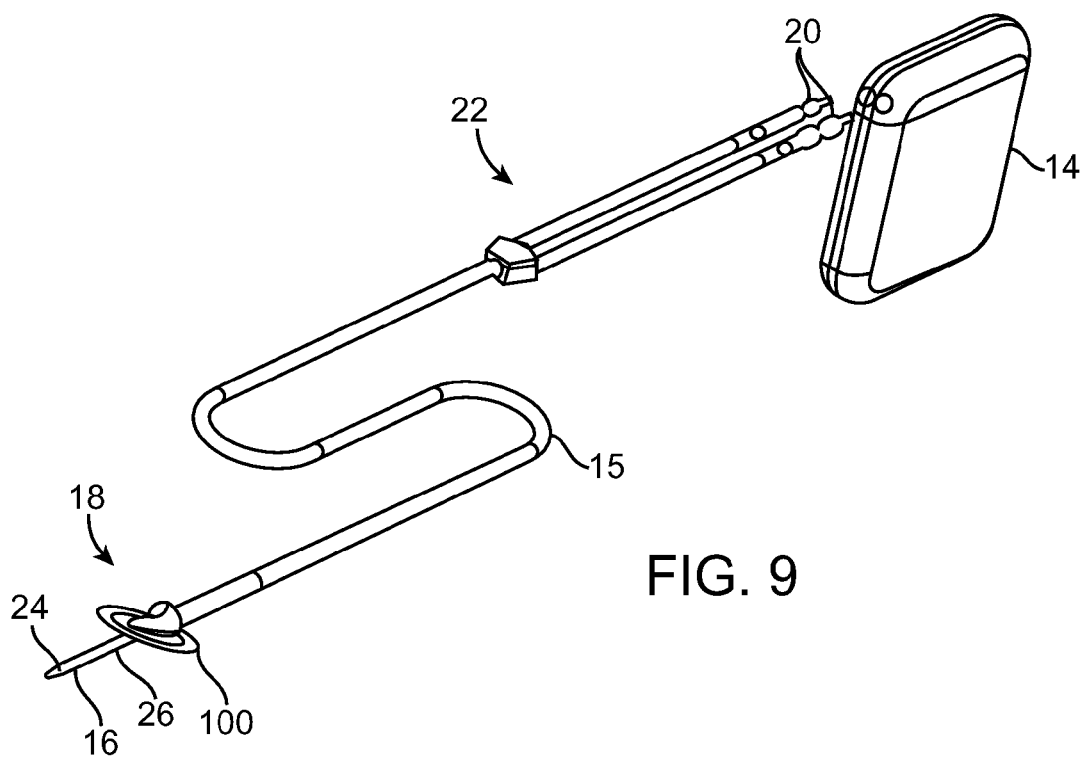
FIG. 9 illustrates another embodiment of a lead of the present invention.

FIG. 9 illustrates another embodiment of a lead 12 of the present invention. As shown, the lead 12 includes a distal end 18 having a transgastric probe 16 and a proximal end 22 having at least one connector 20 which connects with a pulse generator 14. In this embodiment, the transgastric probe 16 is comprised of a polymer, a polytetrafluoroethylene, a flexible polymer, a fluorosilicone, or a perfluoro elastomer, such as Kalrez® and Viton®, or other similar material. The material is chosen to withstand the corrosive environment of the stomach. The probe 16 also includes a sensor 24. Again, it may be appreciated that more than one sensor may also be used. In this example, the sensor 24 senses temperature in the area of the probe 16. Other aspects of the probe will be described in more detail in later sections. In this embodiment, the stimulating electrode 26 is disposed along the transgastric probe 16. Therefore, in this embodiment, stimulation occurs near the sensing site. In addition, the lead body 15 is comprised of an elongate structure having conductive wires passing therethrough or therealong to couple the various sensors and electrodes disposed along the lead 12 to the connectors 20 and then to the pulse generator 14. As shown, this embodiment also includes a suture disc 100. The suture disc 100 is secured to the stomach wall and provides, among other features, stabilization and fixation at the transgastric site. The suture disc 100 will be described in more detail in later sections.

Figure 10:
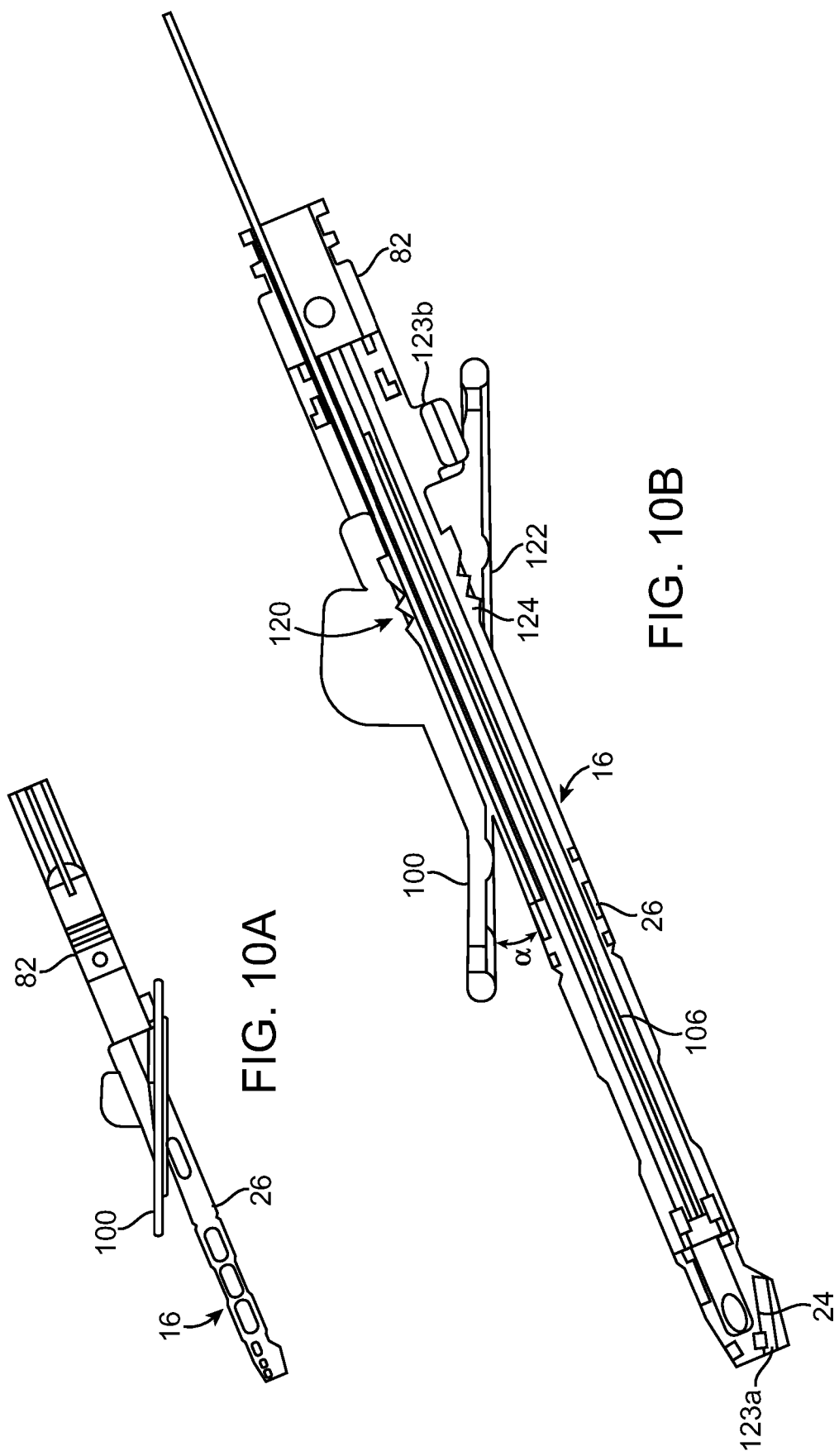
FIGS. 10A-10B provide various views of an embodiment of a polymer transgastric probe.

FIGS. 10A-10B provide various views of the polymer transgastric probe 16. FIG. 10A provides a side view of the probe 16 inserted through the suture disc 100. At least one stimulation electrode 26 is positioned along the probe 16 so as to reside within the transgastric pathway of the stomach wall W once implanted. Thus, the at least one stimulation electrode 26 is distal to the suture disc 100 which rests against the outer surface of the stomach wall W. A return electrode 82 is disposed elsewhere; in this embodiment, the return electrode 82 is shown just proximal of the suture disc 100, and may be in contact with stomach tissue. Optionally, the return electrode 82 can be placed a distance away from the stimulation electrode. In such instances, the return electrode 82 may not be in contact with stomach tissue but rather be in contact with the stomach's omentum, visceral organs or the viscera itself.

FIG. 10B provides a cross-sectional view of the probe 16 of FIG. 10A. As shown, the probe 16 has a sensor 24 disposed within its distal tip. In this embodiment, the probe 16 includes guidewire tracking channels 123a, 123b. One channel 123a is disposed near the distal tip and another channel 123b is disposed proximal to the suture disc 100. The probe 16 may be tracked over a guidewire which passes through these channels 123a, 123b for advancement and delivery of the probe 16 through the gastric wall. In this embodiment, the sensor 24 comprises a glass bulb thermistor with platinum iridium connection wires 102, as illustrated in the detailed view of FIG. 11. The connection wires 102 are laser welded to transition tubes 104 and then to cables 106. A polyimid tubing 108 insulates the bulb and is filled with sealant, compound or potting material 110, such as epoxy. Such sealant acts as a heat conductor. The thermistor subassembly (FIG. 11) is encased in the polymer material of the transgastric probe 16, and such encasing extends proximally beyond the position of the suture disc 100 (and therefore beyond the outer surface of the stomach wall W) so that the thermistor is protected from any possible leakage of gastric secretions or acid from the stomach environment.

FIG. 12 illustrates the transgastric probe 16 of FIG. 10B transecting the stomach wall W. The probe 16 has an elongate cylindrical portion 60 which allows sufficient extension of the cylindrical portion 60 through the stomach wall W and into the stomach cavity. Typically, the cylindrical portion 60 has a length in the range of approximately 15 mm to 25 mm and a diameter in the range of approximately 2 to 5, with a preferred embodiment of 3 mm, but these dimensions are not so limited. Such dimensions are chosen to allow sufficient extension of the cylindrical portion 60 through the stomach wall and into the stomach cavity. In some embodiments, the cylindrical portion 60 has a length in the range of approximately 130-370 mm. Such an extended length may be desired so that the sensor 24 may be positioned where food accumulates within the stomach. In addition, the cylindrical portion 60 has an atraumatic tip, such as having a smooth, rounded shape, to reduce any possibility of injury to the stomach lining as it protrudes through the wall. As shown, the electrodes 26 are positioned along the cylindrical portion 60 so as to contact the stomach wall W, typically residing within the transgastric path.

As shown, a portion of the suture disc 100 rests against the outer surface of the stomach wall W. This allows the disc 100 to orient the transgastric probe 16 through the wall W at a desired angle α. FIGS. 13-14 illustrate the probe 16 passing through the suture disc 100. In this embodiment, the suture disc 100 includes a flange 101 and a guided passageway 103 therethrough. The flange 101 has a flat, circular shape, but it may be appreciated that the flange may have any suitable shape, thickness or contour. The flange 101 may assist in blocking seepage of gastric fluids from the stomach and through the transgastric tract. FIG. 13 provides a top perspective view of the suture disc 100 wherein the guided passageway 103 includes a covering 105 which covers a portion of the elongate cylindrical portion 60 of the probe 16. FIG. 14 provides a bottom perspective view of the suture disc 100 showing the outlet of the guided passageway 103. The suture disc 100 is typically compliant and conforming to the motions and dynamics of the stomach wall.

Referring back to FIG. 10B, the transgastric probe 16 is removably lockable to the suture disc 100 by a locking feature 120. In this embodiment, the locking feature 120 comprises grooves 122 in the guided passageway 103 of the suture disc 100 which mate with ribs 124 along the outer surface of the transgastric probe 16. The ribs 124 are flexible and angled to allow advancement of the transgastric probe 16 through the suture disc 100 until the ribs 124 engage the grooves 122, wherein the probe 16 is fixed in relation to the suture disc 100. In this embodiment the probe 16 is disposed at approximately a 22 degree angle in relation to the suture disc 100. Typically, the angle α ranges from approximately 15 to 45 degrees, however an angle α up to and including 90 degrees may be used. This range of angles allows the lead body 15 to lay closer to the outer surface of the stomach near the transgastric probe 16 and have less interference with surrounding tissues and organs.

The suture disc 100 is attached to the stomach wall W by any suitable technique. Typically, the disc 100 is sutured to the tissue of the wall W. The disc 100 may be comprised of a mesh or penetratable material such that a suturing needle may pass through at any location and sutures placed therethrough. Alternatively or in addition, the suture disc 100 may include one or more suture holes 130, as shown in FIG. 15, which are positioned around the flange 101 and extend therethrough. The flange 101 may then be sutured by passing sutures through the suture holes 130. FIG. 16 provides a top view illustration of a suture disc 100, wherein sutures 131 are shown attaching the disc 100 to the stomach wall W. It may be appreciated that the suture disc 100 may be secured by other fixation methods or anchors, such as staples, clips, adhesives, etc. In some embodiments, the suture disc is attached to the wall of the stomach and then the probe is delivered through the suture disc and fixed in place, such as by snapping into place.

In some embodiments, the suture disc 100 is integrated with the lead body 15 and passed through a laparoscopic port or delivery catheter, such as by folding of the suture disc 100. In other embodiments, the suture disc 100 is separate from the lead body 15 and is sutured to the stomach wall first. Then the transgastric path is created therethrough, followed by a guidewire directed stimulation lead. The lead body 15 is then inserted through the pre-sutured disc 100 and mechanically locked together to affix the stimulation electrode 26 in relation to the stomach wall W. These steps are illustrated in FIGS. 17A-17G.

Referring to FIG. 17A, a laparoscopic port 140 is positioned through the skin SK of the patient, such as in a manner consistent with conventional laparoscopic procedures. A plurality of sutures 142 are placed through the port 140 and advanced through the peritoneal cavity to the stomach wall W. Suture needles 144 at the distal ends of the sutures 142 pass through the stomach wall W in a stitch configuration around a target location 146. The target location 146 indicates the desired location of the transgastric pathway. Referring to FIG. 17B, the suture disc 100 is advanced toward the port 140, the sutures 142 passing through suture holes 130. The suture needles 144 are then passed back up through the port 140. Referring to FIG. 17C, the suture disc 100 is advanced through the port 140 and guided to the target location 146 by the sutures 142. If the suture disc 100 is flexible or pliable, the suture disc 100 may be rolled up and inserted through a smaller profile port, and with a plunger the suture disc 100 is passed into the peritoneal cavity. The use of smaller profile ports allows a less invasive surgery with smaller access wounds, speedier recovery and cosmetic benefits.

Referring to FIG. 17D, the transgastric path is then formed through an opening 148 in the suture disc 100 which is positioned over the target location 146. The opening 148 serves as centering jig for advancement of a needle 150, guidewire 151, and optionally a dilation balloon 152. FIG. 17D illustrates dilation of the transgastric pathway by inflation of a dilation balloon 152. However, it may be appreciated that such dilation is optional; the transgastric pathway need only be large enough for passage of the transgastric probe 16 therethrough.

Figure 17E:
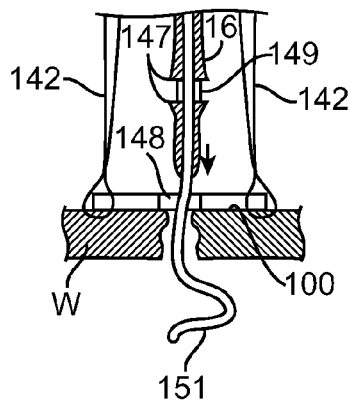
Figure 17F:
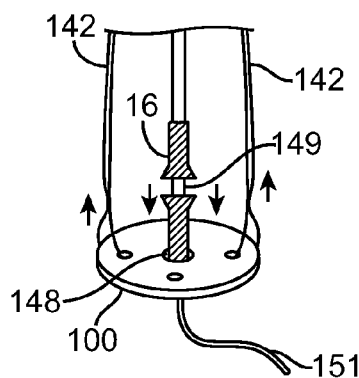
Figure 17G:
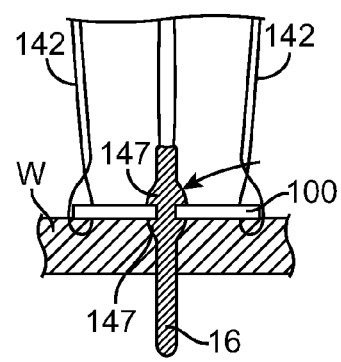

Referring to FIG. 17E, knots may be tied with the free suture ends and advanced down the suture lines 142 with a knot pusher so that the suture disc 100 is secured in place. The sutures 142 remain in place and are used as tension lines to oppose tool or lead insertion forces. The transgastric probe 16 is advanced over the guidewire 151 toward the opening 148. Referring to FIG. 17F, the probe 16 is advanced through the opening 148. In this embodiment, the probe 16 is shaped to include a notch 149 between small flanges 147. The probe 16 is advanced until the notch 149 aligns with the opening 148, as shown in FIG. 17G. This allows the flanges 147 to straddle the suture disc 100 and seal the opening 148. Such sealing minimizes any possible gastric contamination through the transgastric path. Also, the transgastric probe 16 is mechanically locked to the suture disc 100. The lead 12 cannot translate in or out of the stomach wall W, given that the suture disc 100 is fixed to the stomach wall W and the suture disc 100 is locked to the notch 149 of the transgastric probe 16.

Figure 18:
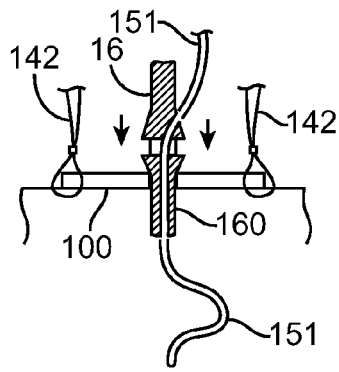
FIGS. 18, 19, 20 illustrate alternative embodiments of mechanically locking a transgastric probe to a suture disc.
Figure 19:
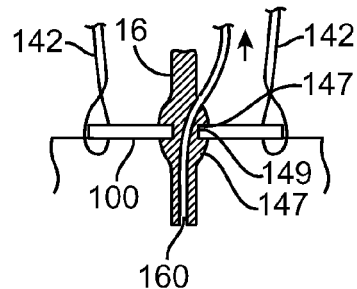
Figure 20:
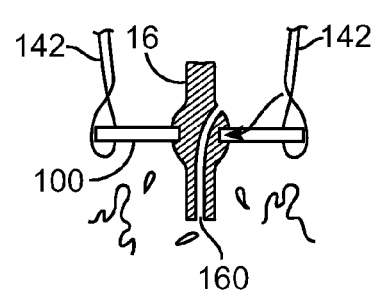

FIGS. 18-20 illustrate alternative embodiments of mechanically locking the transgastric probe 16 to the suture disc 100. FIG. 18 illustrates a transgastric probe 16 having a guidewire lumen 160 extending from its side toward its distal tip. FIG. 19 shows the transgastric probe 16 advanced through the opening 148 so that the notch 149 aligns with the opening 148 and the flanges 147 straddle the suture disc 100 to seal the opening 148. The guidewire lumen 160 may then be sealed by advancing a sealing sleeve or band over the probe 16 so as to obstruct the opening of the guidewire lumen 160. FIG. 20 illustrates a similar embodiment. However, in this embodiment, the guidewire lumen 160 extends through the transgastric probe 16 so that it passes through the notch 149. Thus, alignment of the notch 149 with the opening 148 obstructs or causes the suture disc 100 to seal off the guidewire lumen 160 when locked in coupled arrangement.

A suture disc 100 which is separate from the lead body 15 provides a variety of advantages. To begin, each element may be deployed separately through a small cannula or laparoscopic port which is smaller than the standard 12 mm inner diameter. The separate suture disc 100 also provides ease of precisely affixing the suture disc 100 to the stomach wall W with little stress on the tissue and intimate sealing of the suture disc 100 to the wall W. This may allow a wider range of skilled physicians to position the transgastric probe 16. Laparoscopic suturing is not difficult for skilled laparoscopic surgeons, however suturing multiple points around a suture disc 100 may be more challenging for some surgeons, particularly if the view is obstructed by an integrally attached lead. This may increase procedure time which increases the time that the patient is under anesthesia. Thus, a separate suture disc 100 that is guided down to the stomach wall W via suture lines as described may reduce the challenges stated above. In addition, a separate suture disc 100 may seal off a guidewire lumen through the transgastric probe 16 to prevent migration of contaminants or flora into the peritoneum.

The pre-sutured disc 100 may also be used for tissue management during introduction of the transgastric probe 16. The plurality of sutures 142 affixing the suture disc 100 against the stomach wall W can be tensioned through the laparoscopic port 140 to elevate the stomach wall W or support the disc 100 while advancing various tools across the stomach wall W so as to reduce injury to the inside of the stomach if passed too far. In addition, it may be desirable to position the lead with the stomach in a desufflated or low pressure insufflated state to minimize contamination across any transgastric paths. In such instances, the sutures 142 may also act as tenting lines.

An additional attribute of the separate suture disc 100 is that the transgastric probe 16 may be easily removed from the stomach wall W by disengaging the probe 17 from the disc 100, rather than unsuturing an integrally formed suture disc 100. By applying sufficient tension to the proximal end of the lead 12, the notch 149 may be disengaged from the opening 148 and separated from the sutured disc 100. The sutured disc 100 may remain adhered to the stomach wall W leaving a transgastric path that would heal.

Figure 21A:
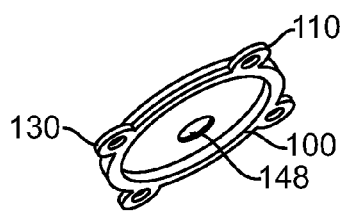
FIGS. 21A-21C illustrate advancement through and locking of a probe to a suture disc.
Figure 21B:
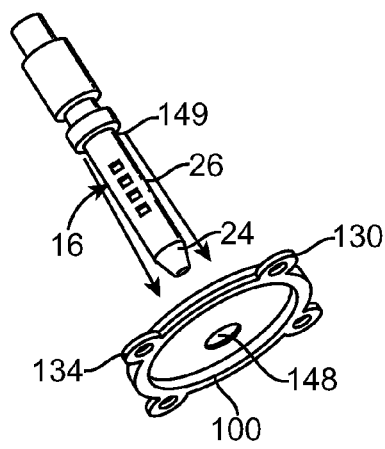
Figure 21C:
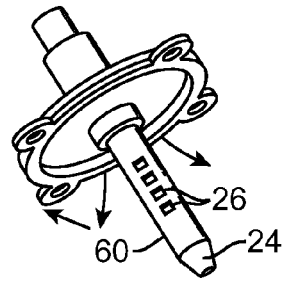

It may be appreciated that the suture discs 100 may have a variety of sized, shaped or positioned suture holes 130. Further, such suture holes 130 may be formed around the exterior of the disc 100, such as in the form of eyelets, as shown in FIG. 21A. FIG. 21B illustrates a transgastric probe 16 advancing toward the opening 148 in the suture disc 100. And FIG. 21C illustrates the notch 149 locked with the disc 100 and the elongate portion 60 of the probe 16 extending therethrough.

Figure 22A:
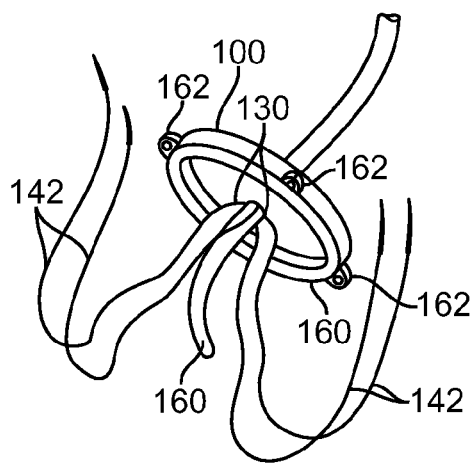
FIGS. 22A-22D illustrate an embodiment of a suture disc which actively seals against the stomach wall to assist in fixation.
Figure 22B:
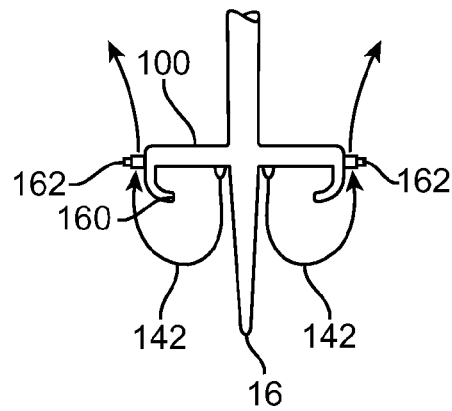
Figure 22C:
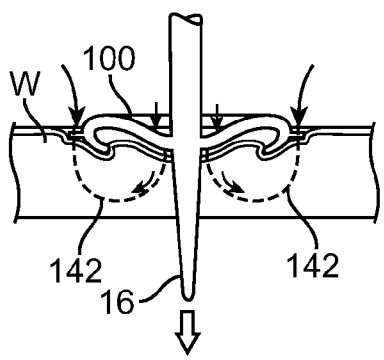
Figure 22D:
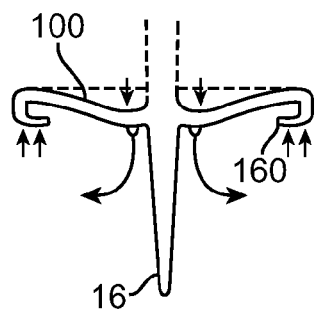

FIGS. 22A-22D illustrate an embodiment of a suture disc 100 which actively seals against the stomach wall W to assist in closure of the transgastric path so as to prevent leakage of stomach fluids through the transgastric path. In this embodiment, the suture disc 100 is integral with the transgastric probe 16, however the suture disc 100 may alternatively be separate and lockable to the probe 16. Referring to FIG. 22A, the suture disc 100 has a plurality of suture holes 130 near the center of the disc 100 around the probe 16. The suture disc 100 also has a concave configuration wherein a lip 160 is formed at least partially around the disc 100. Sutures 142 extend in a distal direction through the holes 130 and then loop backwards, passing in a proximal direction through eyelets 162 around the perimeter of the disc 100, as illustrated in FIG. 22B. When the disc 100 is positioned against the stomach wall W, as illustrated in FIG. 22C, the sutures 142 pass through the stomach wall W and exit through the eyelets 162. Applying tension to the sutures 142 draws the center of the disc 100 downward against the stomach wall W, as indicated by arrows in FIGS. 22C-22D. The buckling of the suture disc 100 and the lip 160 creates suction and seals the tissue up against the probe 16.

Figure 23A:
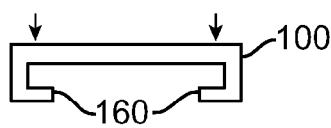
FIGS. 23A-23B and FIGS. 24A-24B illustrate various lip designs.
Figure 24A:
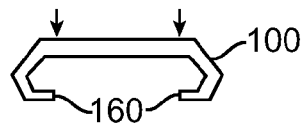
Figure 23B:
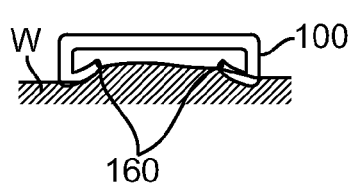
Figure 24B:
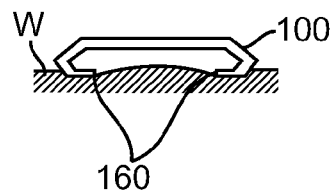

The lip 160 of the disc 100 may have a variety of shapes, sizes and configurations to maximize sealing area. For example, FIG. 23A illustrates a disc 100 having a lip 160 which extends in a square configuration in free space. When the lip 160 contacts the stomach wall W, as illustrated in FIG. 23B, and tension is applied to the sutures (not shown), the lip 160 conforms to the stomach wall W increasing downward force to the lip 160 of the disc 100, thus imparting a sealing "ring" onto the serosal surface of the stomach. Similarly, FIGS. 24A-24B illustrate another embodiment of a disc 100 having a shaped lip 160.

Figure 26F:
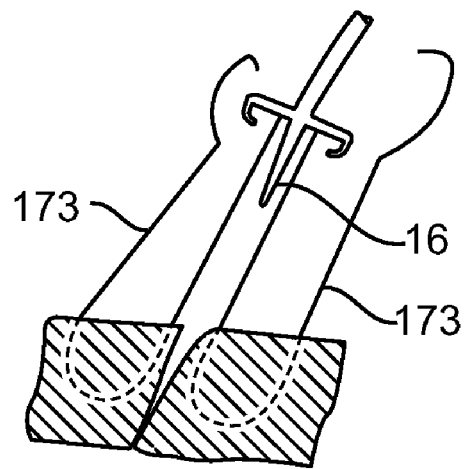
FIG. 26F illustrates a gastric probe advanced over the sutures positioned with the use of a needle delivery tool.

To assist in positioning the sutures 142 in the embodiment illustrated in FIGS. 22A-22D, a needle delivery tool 170 may be used. FIGS. 25A-25B illustrate an embodiment of a needle delivery tool 170. In this embodiment, the tool 170 includes a plurality of pre-curved needles 172 arranged around a shaft 174. The needles 172 are coverable by a retractable sheath 176. Advancement of the sheath 176 draws the needles 172 toward the shaft 174, as illustrated in FIG. 25A. Retraction of the sheath 176 reveals and releases the needles 172 which allows the needles 172 to curve radially outwardly as shown in FIG. 25B. FIGS. 26A-26E illustrate the needle delivery tool 170 in use. In FIG. 26A, the needles 172 are covered by the sheath 176 as the tool 170 is advanced toward a target location 178 on the stomach wall W. The tool 170 is then advanced transgastrically into the stomach wall W, as illustrated in FIG. 26B. Once desirably positioned within the stomach wall W, the sheath 176 is retracted as illustrated in FIG. 26C. As the sheath 176 is retracted the needles 172 curve radially outwardly in a proximal direction as illustrated in FIG. 26D. The sheath 176 is then rotated to release the needles 172 (and sutures 173 thereattached) from the tool 170. It may be appreciated that the sheath 176 may alternatively be comprised of separable halves that separate to release the sutures 173 or a tear-away sheath that tears to release the sutures 173. FIG. 26F shows a gastric probe 16 advanced over the sutures 173.

Figure 27:
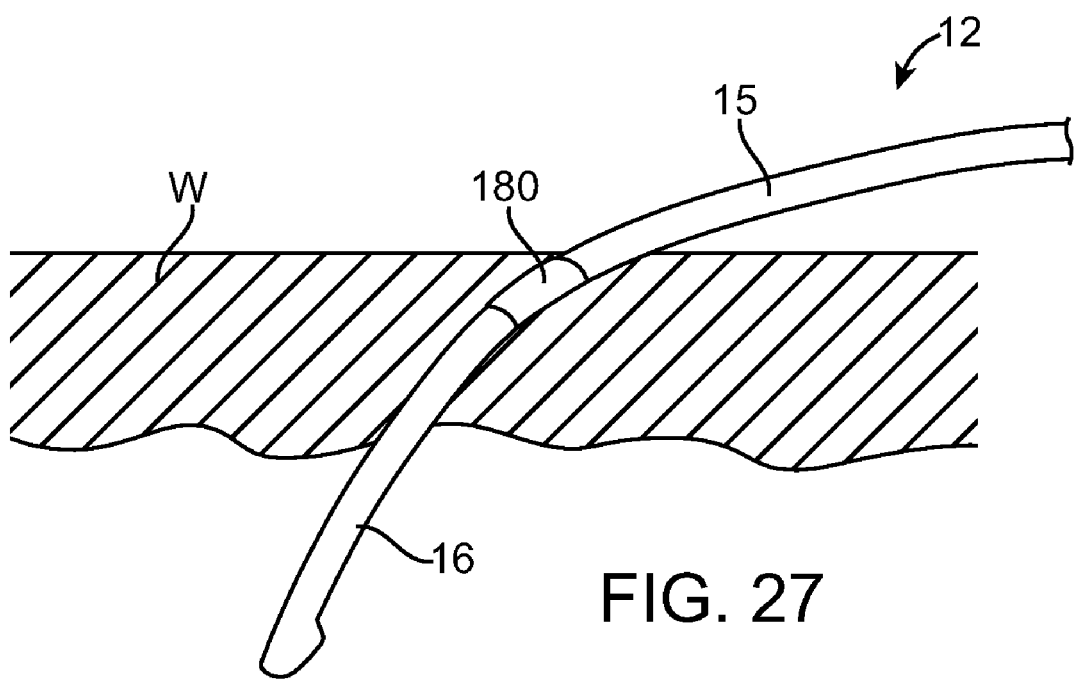
FIG. 27 illustrates an embodiment of an ingrowth cuff positioned around a lead body near a transgastric probe.

In some embodiments, an ingrowth cuff is used as an alternative to the suture disc 100 to anchor the transgastric probe 16 to the stomach wall W. Such a cuff typically has the form of a circumferential band of porous or textured material around the lead body 15. FIG. 27 illustrates an example of such a cuff 180 positioned around the lead body 15 near the transgastric probe 16. Example materials include veloured polyester mesh, polytetrafluoroethylene (PTFE) felt, or other implantable polymer textiles. Likewise, a cuff as utilized on Tenckhoff catheters may be adapted for use with the present invention. Over time, the stomach tissue grows into the ingrowth cuff, sealing the transgastric path and anchoring the lead 12 in place.

Delivery Tools and Surgical Approach

Although some of the above descriptions have mentioned laparoscopic techniques and methods, it may be appreciated that a variety of surgical approaches may be used when approaching the stomach wall from the outside. Examples include a laparoscopic approach, a percutaneous endoscopic gastrostomy (PEG) approach or a modified PEG approach, such as described in U.S. Provisional Application No. 60/821, 370, filed Aug. 3, 2006, incorporated herein by reference for all purposes. These different approaches may use various levels of insufflation, and in some cases avoiding insufflation altogether. It may be appreciated that any of these techniques may be used in conjunction with the present invention.

By means of example, methods of utilizing the present invention with a laparoscopic approach will be described herein. The described method is merely one embodiment and is not intended to limit the scope of the present invention. To begin, the patient is prepped according to conventional laparoscopic procedures. In addition, the stomach may be lavaged prior to the implantation procedure with an antiseptic, antibiotic/antimicrobial solutions, or a combination thereof to reduce the risk of infection to the peritoneal cavity from the formation of the transgastric path. These solutions may also be additional used to wash the target site directly via an endoscopic tool port and syringe. At least two laparoscopic ports or cannulae are placed through the skin into the abdomen; one cannula used for introduction of a laparoscope and one cannula used for delivery of the lead. At least two laparoscopic ports or cannulae are also placed bilateral to the laparoscope cannula. The abdominal cavity is generally insufflated with $CO_2$ gas and often a muscle relaxant is recommended to increase distension of the insufflated cavity and increase visibility The target site for the stimulation electrode is then determined, such as on the anterior mid-body near the pes anserinus. Likewise the target site for the transgastric probe is determined, such as near the greater curvature in the mid-body region. It may be appreciated that the transgastric probe may be inserted at any position along the stomach.

The lead is delivered into the peritoneal cavity through one of the laparoscopic cannulae, optionally with the assistance of a laparoscopic grasper. The stimulation electrode and transgastric probe are then fixed at their designated target locations, in either order. The stimulation electrode may be sutured in place with the use of anchoring features. The transgastric probe may be fixed in place by a variety of techniques. After securing the initial purse string suture to acutely seal the gastric wall against the probe, a second larger purse string suture may be placed around the target site. Upon applying tension to this outer purse string, the gastric tissue may be urged up and over the top of the suture disc, enveloping it and securely maintaining the probe's transgastric implant position. Positioning across the gastric wall can be achieved with the use of a variety of tools, such as with the use of a needle or a radiofrequency or cautery tool create the transgastric pathway. Or, a transgastric dilator tool may be used that incorporates a tip that is sharp and mimics a needle but dilates to a size greater than the diameter of the distal portion of the lead.

The proximal end of the lead 22 is extended through a tract in the peritoneum to a subcutaneous location that will become the implant site for the gastric pulse generator 14. The connectors are inserted into a respective set of receptacles in the pulse generator header and secured in place. A subcutaneous tissue pocket is prepared against the muscular fascia, and the pulse generator is secured to the fascia such as with suture. All cannulae are removed and all incisions are closed.

It may be appreciated that the methods will be modified depending on the features of a particular embodiment. For example, for lead system embodiments having stimulation electrodes only on the transgastric probe, the steps of positioning the stimulation electrodes at a separate location will be eliminated. Likewise, for lead system embodiments without a suture disc, steps involving the suture disc will be eliminated. And, for lead system embodiments having additional anchoring features, additional steps will be included to actuate such features.

The lead systems and methods of the present invention have been described in relation to the gastric anatomy, particularly the stomach. It may be appreciated that the lead systems and methods may be used to stimulate and/or sense information in relation to other organs. For example, the transgastric probe may be inserted through a tissue or organ wall other than a stomach wall, such as a bladder, duodenum or esophagus. And the stimulation electrode may be positioned so as to stimulate the same or another tissue or organ wall.

Although the foregoing invention has been described in some detail by way of illustration and example, for purposes of clarity of understanding, it will be obvious that various alternatives, modifications and equivalents may be used and the above description should not be taken as limiting in scope of the invention which is defined by the appended claims.

What is claimed is:

1. A lead for stimulating a stomach having an internal cavity, the lead comprising:
   a lead body having a distal end;
   a transgastric probe disposed near the distal end of the lead body, the probe configured to be implanted across a wall of the stomach so that the probe extends into the internal cavity; and
   at least one electrode disposed along the lead body proximally separated from the transgastric probe, wherein the at least one electrode is configured to be implanted in the patient on an outer surface of the stomach so as to be in electrical contact with the wall of the stomach at a location along the lead body proximally separated from the transgastric probe such that the lead has sufficient slack between the at least one electrode and transgastric probe to accommodate changes in the stomach when implanted.

2. A lead as in claim 1, wherein the transgastric probe includes a sensor configured to sense an aspect of the internal cavity.

3. A lead as in claim 2, wherein the sensor comprises a temperature sensor.

4. A lead as in claim 1, wherein the lead body includes an anchoring feature which is attachable to the stomach wall so as to anchor the at least one electrode in engagement with the wall.

5. A lead as in claim 1, wherein the probe has an outer surface exposed to the internal cavity during implantation wherein the outer surface primarily comprises a conductive material.

6. A lead as in claim 5, wherein the probe is configured to act as a return electrode.

7. A lead as in claim 1 further comprising a suture disc disposed along the lead body, wherein the suture disc is positioned so as to be attached to the wall of the stomach while the transgastric probe is implanted.

8. A lead as in claim 7, wherein the suture disc positions the probe at an angle of less than approximately 90 degrees relative to the wall.

9. A lead as in claim 7, wherein the suture disc is removable.

10. A lead as in claim 1, further comprising a buffer disc positionable near the wall while the probe is implanted so as to assist in sealing a transgastric path made by the probe.

11. A lead as in claim 10, wherein the buffer disc comprises a tissue adhering material.

12. A lead as in claim 1, wherein the probe has an outer surface exposed to the internal cavity during implantation wherein the outer surface primarily comprises a polymer, a flexible polymer, a perfluoro elastomer or a combination of these.

13. A system for stimulating a stomach having an internal cavity, the system comprising:
   a lead having a distal end and a proximal end;
   a transgastric probe disposed near the distal end, the probe configured to be implanted across a wall of the stomach so that the distal end extends into the internal cavity during implantation;
   a suture disc removably coupleable with the lead so that the suture disc is attachable to the stomach wall while the transgastric probe is implanted; and
   at least one electrode disposed along the proximal end of the lead, wherein the at least one electrode is proximally separated from the transgastric probe and wherein the proximal end engages an outer surface of the stomach so as to be in electrical contact with an outer wall of the stomach at a location along the lead separated from the transgastric probe such that the lead has sufficient slack between the at least one electrode and transgastric probe to accommodate changes to the stomach when the probe is implanted.

14. A system as in claim 13, wherein the at least one electrode is disposed along the gastric probe.

15. A system as in claim 13, wherein the at least one electrode is disposed proximal to the gastric probe.

16. A system as in claim 13, wherein the transgastric probe includes a sensor configured to sense an aspect of the internal cavity.

17. A system as in claim 16, wherein the sensor comprises a temperature sensor.

18. A system as in claim 13, wherein the suture disc is foldable for delivery through a delivery device.

19. A system as in claim 13, wherein the suture disc positions the probe at an angle of less than approximately 90 degrees relative to the wall.

20. A system as in claim 13, wherein the suture disc obstructs a passageway through at least a portion of the lead when locked in coupled arrangement with the lead.

21. A method of stimulating a stomach having an internal cavity comprising:
  advancing a lead toward an outer surface of the stomach, the lead having a transgastric probe and at least one electrode, wherein the at least one electrode is proximally separated from the transgastric probe along the lead;
  implanting the transgastric probe across a wall of the stomach so that a distal tip of the transgastric probe extends into the internal cavity and a proximal portion of the transgastric probe engages the outer surface of the stomach;
  affixing the at least one electrode to the outer surface of the stomach so as to be in electrical contact with the wall of the stomach at a location separated from the implanted transgastric probe, wherein the lead has sufficient slack between the at least one electrode and probe to accommodate changes to the stomach; and
  cinching the wall of the stomach against the transgastric probe.

22. The method of claim 21, wherein the at least one electrode is disposed along the lead proximal to the transgastric probe near an anchoring feature, and wherein engaging the at least one electrode comprises attaching the anchoring feature to the outer surface of the organ.

23. The method of claim 21, wherein cinching comprises placing a purse string suture around the transgastric probe.

24. The method of claim 21, wherein implanting the transgastric probe comprises implanting the probe across the wall near a greater curvature of the stomach.

25. The method of claim 24, wherein engaging the at least one electrode with the wall comprises engaging the wall in a zone near a lesser curvature of the stomach.

26. The method of claim 21, further comprising joining the lead with an implantable pulse generator.

27. The method of claim 21, wherein advancing the lead comprises approaching the outer surface of the organ with a laparoscopic approach.

28. The method of claim 21, wherein advancing the lead comprises approaching the outer surface of the organ with a percutaneous endoscopic gastrostomy approach or a modified percutaneous endoscopic gastrostomy approach.

29. The method of claim 21, wherein the at least one electrode is configured to be implanted in the wall so as to be in electrical contact with the wall at a location along the lead separated from the transgastric probe such that the at least one electrode engages the wall.

* * * * *